United States Patent
Comee et al.

(10) Patent No.: US 12,342,983 B2
(45) Date of Patent: Jul. 1, 2025

(54) MOTION TRANSLATION AND INTERFACE DEVICES, SYSTEMS, AND METHODS FOR ENDOSCOPE VALVES

(71) Applicant: Boston Scientific Scimed, Inc., Maple Grove, MN (US)

(72) Inventors: Shaun D. Comee, Fiskdale, MA (US); Paula R. Limberg, Northborough, MA (US); Laura E. Richards, Westfield, IN (US); Rossana Zotti, Miami, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/482,226

(22) Filed: Oct. 6, 2023

(65) Prior Publication Data
US 2024/0032774 A1 Feb. 1, 2024

Related U.S. Application Data

(63) Continuation of application No. 17/208,772, filed on Mar. 22, 2021, now Pat. No. 11,812,927.
(Continued)

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/015* (2013.01); *A61B 1/12* (2013.01);
(Continued)

(58) Field of Classification Search
CPC ............ A61B 1/00068; A61B 1/00082; A61B 1/00091; A61B 1/00094; A61B 1/00119;
(Continued)

(56) References Cited

U.S. PATENT DOCUMENTS 4,061,250 A * 12/1977 Tada ................... B05B 11/1014
251/321
4,694,821 A * 9/1987 Kondo ............... A61B 1/00068
600/158

(Continued)

FOREIGN PATENT DOCUMENTS

EP 2431062 A1 3/2012
JP 2000217777 A 8/2000
(Continued)

OTHER PUBLICATIONS

International Search Report and Written Opinion for the International Patent Application No. PCT/US2021/023478, dated Jun. 10, 2021, 49 pages.

(Continued)

*Primary Examiner* — Ryan N Henderson
(74) *Attorney, Agent, or Firm* — Seager, Tufte & Wickhem, LLP

(57) ABSTRACT

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable.

11 Claims, 33 Drawing Sheets

Related U.S. Application Data

(60) Provisional application No. 62/994,024, filed on Mar. 24, 2020, provisional application No. 62/994,019, filed on Mar. 24, 2020, provisional application No. 62/994,021, filed on Mar. 24, 2020, provisional application No. 62/994,015, filed on Mar. 24, 2020, provisional application No. 62/994,018, filed on Mar. 24, 2020, provisional application No. 62/994,008, filed on Mar. 24, 2020.

(51) Int. Cl.
*A61B 1/12* (2006.01)
*F16K 21/20* (2006.01)
*A61B 1/018* (2006.01)

(52) U.S. Cl.
CPC .......... *F16K 21/20* (2013.01); *A61B 1/00082* (2013.01); *A61B 1/018* (2013.01)

(58) Field of Classification Search
CPC . A61B 1/00128; A61B 1/00137; A61B 1/015; A61B 1/018; A61B 1/12; A61B 1/126; A61B 1/127; F16K 21/20
See application file for complete search history.

(56) References Cited

U.S. PATENT DOCUMENTS

| | | | | | |
|---|---|---|---|---|---|
| 4,800,869 | A | * | 1/1989 | Nakajima | A61B 1/00068 600/158 |
| 5,027,791 | A | * | 7/1991 | Takahashi | A61B 1/126 600/158 |
| 5,938,589 | A | * | 8/1999 | Wako | A61B 1/12 200/5 B |
| 6,334,844 | B1 | * | 1/2002 | Akiba | A61B 1/00068 600/156 |
| 6,346,075 | B1 | | 2/2002 | Arai et al. | |
| 8,568,303 | B2 | * | 10/2013 | Yamane | A61B 1/12 600/156 |
| 9,161,680 | B2 | * | 10/2015 | Bellofatto | A61B 1/0011 |
| 2010/0049001 | A1 | * | 2/2010 | Yamane | A61B 1/015 600/159 |
| 2011/0208003 | A1 | * | 8/2011 | Yamane | A61B 1/12 600/159 |
| 2011/0298169 | A1 | * | 12/2011 | Nguyen | A61B 1/125 269/86 |
| 2012/0085956 | A1 | * | 4/2012 | Morimoto | A61B 8/445 251/324 |
| 2012/0088973 | A1 | * | 4/2012 | Morimoto | A61B 1/00068 600/156 |
| 2012/0088975 | A1 | * | 4/2012 | Morimoto | A61B 1/00068 600/159 |
| 2015/0144215 | A1 | * | 5/2015 | Bellofatto | F16K 11/0712 137/625.69 |
| 2015/0148608 | A1 | * | 5/2015 | Fukushima | A61B 1/00094 600/116 |
| 2016/0302646 | A1 | * | 10/2016 | Hamazaki | A61B 1/00 |
| 2018/0361034 | A1 | * | 12/2018 | Tobien | F16K 31/5245 |
| 2019/0125167 | A1 | * | 5/2019 | Taniguchi | A61B 1/015 |
| 2019/0350441 | A1 | * | 11/2019 | Saiga | A61B 1/00068 |
| 2019/0350444 | A1 | * | 11/2019 | Saiga | A61B 1/00068 |
| 2019/0350445 | A1 | * | 11/2019 | Saiga | G02B 23/2476 |
| 2019/0350446 | A1 | * | 11/2019 | Saiga | A61B 1/00068 |
| 2020/0016637 | A1 | * | 1/2020 | Still | A61B 1/125 |
| 2020/0187756 | A1 | * | 6/2020 | Maurice | A61B 1/126 |
| 2020/0355281 | A1 | * | 11/2020 | Harris | F16K 11/0716 |
| 2020/0375434 | A1 | * | 12/2020 | Scutti | A61B 1/00068 |
| 2020/0386330 | A1 | * | 12/2020 | Stanton | A61M 39/16 |
| 2021/0007586 | A1 | * | 1/2021 | Gavalis | A61B 1/125 |
| 2021/0076914 | A1 | * | 3/2021 | Arai | G02B 23/24 |

FOREIGN PATENT DOCUMENTS

| | | |
|---|---|---|
| JP | 2007111266 A | 5/2007 |
| WO | 2019225562 A1 | 11/2019 |

OTHER PUBLICATIONS

International Search Report and Written Opinion for the International Patent Application No. PCT/US2021/023479, dated Jul. 9, 2021, 12 pages.

International Search Report and Written Opinion for the International Patent Application No. PCT/US2021/023482, dated Jul. 9, 2021, 12 pages.

International Search Report and Written Opinion for the International Patent Application No. PCT/US2021/023484, dated Jul. 9, 2021, 12 pages.

* cited by examiner

100

SUCTION VALVE ASSEMBLY 102

SUCTION VALVE WELL 104

- SUCTION CHANNEL 106
- WORKING CHANNEL 108
- BALLOON CHANNEL 114
- ATMOSPHERIC CHANNEL 116

SUCTION VALVE SET 118

- WORKING CHANNEL VALVE 120
- BALLOON VALVE 122
- ATMOSPHERIC VALVE 124

VALVE INTERFACE MECHANISM 126

- BIASING MEMBER SET 128
- USER INTERFACE MECHANISM 130

AIR/WATER (AW) VALVE ASSEMBLY 202

AW VALVE SET 204

| AIR INPUT CHANNEL 206 | WATER INPUT CHANNEL 208 | AIR OUTPUT CHANNEL 210 |
|---|---|---|
| WATER OUTPUT CHANNEL 212 | BALLOON CHANNEL 214 | ATMOSPHERIC CHANNEL 216 |

AW VALVE SET 218

| PRIMARY CONTROL VALVE 220 | AIR INPUT VALVE 222 | ATMOSPHERIC VALVE 224 |
|---|---|---|

VALVE INTERFACE MECHANISM 226

| BIASING MEMBER SET 228 | USER INTERFACE MECHANISM 230 |
|---|---|

FIG. 2

MOTION TRANSLATION AND INTERFACE DEVICES, SYSTEMS, AND METHODS FOR ENDOSCOPE VALVES

PRIORITY

This application is a continuation of U.S. patent application Ser. No. 17/208,772, filed Mar. 22, 2021, which claims the benefit of priority to U.S. Provisional Application Ser. No. 62/994,019, filed Mar. 24, 2020, the disclosures of which are hereby incorporated by reference in their entirety.

RELATED APPLICATIONS

This application relates to, and incorporates by reference in its entirety for all purposes, U.S. Provisional Patent Application No. 62/994,008, titled "Interface and Motion Translation Devices, Systems, and Methods for Endoscope Valves", filed Mar. 24, 2020.

This application relates to, and incorporates by reference in its entirety for all purposes, U.S. Provisional Patent Application No. 62/994,015, titled "Devices, Systems, and Methods for Controlling Fluids in Endoscope Systems", filed Mar. 24, 2020.

This application relates to, and incorporates by reference in its entirety for all purposes, U.S. Provisional Patent Application No. 62/994,018, titled "Devices, Systems, and Methods for Endoscope Valve Control", filed Mar. 24, 2020.

This application relates to, and incorporates by reference in its entirety for all purposes, U.S. Provisional Patent Application No. 62/994,021, titled "Devices, Systems, and Methods for Fluid Control in Endoscope Systems", filed Mar. 24, 2020.

This application relates to, and incorporates by reference in its entirety for all purposes, U.S. Provisional Patent Application No. 62/994,024, titled "Devices, Systems, and Methods for Endoscope Fluidics", filed Mar. 24, 2020.

FIELD

The present disclosure relates generally to the field of medical devices. In particular, the present disclosure relates to devices, systems, and methods to control flow through a valve well for an endoscope.

BACKGROUND

An endoscopy procedure is used in medicine to access the interior of a body for diagnostic and/or therapeutic procedures. Oftentimes, the endoscopy procedure uses an endoscope to examine or manipulate the interior of a hollow organ or cavity of the body. Unlike many other medical imaging techniques, endoscopes are inserted directly into the organ. Typically, an endoscope includes one or more channels for the flow of one or more fluids therethrough. For example, one or more of suction, air, and water may flow through an endoscope. A valve assembly may be configured and used in various fashion to control the flow of the one or more fluids through the endoscope. In the case of an echoendoscope or ultrasound endoscope, control of fluids may also be used to inflate and deflate a balloon at the end of an endoscope.

It is with these considerations in mind that a variety of advantageous outcomes may be realized by the devices, systems and methods of the present disclosure.

SUMMARY

In one aspect, the present disclosure relates to a medical device comprising a valve set and a valve interface mechanism. The valve set may include a valve set including a primary control valve, an air input valve, and an atmospheric valve, the primary control valve may be configured to control flow between a water input channel, a water output channel, and a balloon channel of a valve well, the air input valve may be configured to control flow through an air input channel of the valve well, and the atmospheric valve may be configured to control flow through an atmospheric channel. The valve interface mechanism may include a set of one or more biasing members and a user interface mechanism. The user interface mechanism may comprise a toggle coupled to a cam, the toggle may be operable between a first state, a second state, a third state, and a fourth state, the first state may comprise the valve set configured to place the air input channel in fluid communication with the atmospheric channel, the second state may comprise the valve set configured to place the air input channel in fluid communication with the air output channel, the third state may comprise the valve set configured to place the water input channel in fluid communication with the water output channel, and the fourth state may comprise the valve set configured to place the water input channel in fluid communication with the balloon channel. In the first state, the air input valve permits flow through the air input channel and the atmospheric valve permits flow through the atmospheric channel. In the second state, the air input valve permits flow through the air input channel and the atmospheric valve blocks flow through the atmospheric valve. In the third state, the primary control valve permits flow from the water input channel to the water output channel and the air input valve blocks flow through the air input channel. In the fourth state, the primary control valve permits flow from the water input channel to the balloon channel and the air input valve blocks flow through the air input channel. In various embodiments, the cam may translate motion of the toggle into linear motion of the primary control valve. In some embodiments, the cam may comprise a plurality of steps, wherein each of the plurality of steps causes a different amount of linear motion of the primary control valve. In some such embodiments, the plurality of steps may comprise a first step corresponding to the second state, a second step corresponding to the third state, and a third step corresponding to the fourth state. In one or more embodiments, the cam may comprise a plurality of steps, wherein each of the plurality of steps are configured to seal the atmospheric channel. In many embodiments, the toggle is configured to receive input to operate the user interface to one or more of the first state, the second state, the third state, and the fourth state. In several embodiments, the set of one or more biasing members may comprise a first biasing member to bias the primary control valve toward a top of the valve well. In various embodiments, the set of one or more biasing members may comprise a second biasing member to couple the primary control valve to the air input valve. In several embodiments, the set of one or more biasing members may comprise a biasing member to bias the air input valve against the air input channel in the third and fourth states. In some embodiments, the biasing member may prevent the air input valve from blocking the air input channel in the first and second states.

In another aspect, the present disclosure relates to a medical device comprising a valve set and a user interface mechanism. The valve set may include a primary control valve, an air input valve, and an atmospheric valve, the primary control valve may be configured to control flow between a water input channel, a water output channel, and a balloon channel of a valve well, the air input valve may be configured to control flow through an air input channel of the valve well, and the atmospheric valve may be configured to control flow through an atmospheric channel. The valve interface mechanism may include a set of one or more biasing members and a user interface mechanism, the user interface mechanism may comprise an interface member and a slot cam, the interface member may be operable between a first state, a second state, a third state, and a fourth state, the first state may comprise the valve set configured to place the air input channel in fluid communication with the atmospheric channel, the second state may comprise the valve set configured to place the air input channel in fluid communication with the air output channel, the third state may comprise the valve set configured to place the water input channel in fluid communication with the water output channel, and the fourth state may comprise the valve set configured to place the water input channel in fluid communication with the balloon channel. In the first state the air input valve permits flow through the air input channel and atmospheric valve permits flow through the atmospheric channel. In the second state the air input valve permits flow through the air input channel and the atmospheric valve blocks flow through the atmospheric valve. In the third state the primary control valve permits flow from the water input channel to the water output channel and the air input valve blocks flow through the air input channel. In the fourth state, the primary control valve permits flow from the water input channel to the balloon channel and the air input valve blocks flow through the air input channel. In various embodiments, the slot cam may translate rotational motion of the interface member into linear motion of the primary control valve. Several embodiments may comprise a cam pin and a linkage, the linkage may couple the cam pin to the primary control valve. In several such embodiments, the cam pin may follow the slot cam to translate rotational motion of the interface member into linear motion of the primary control valve. Transition from one or more of the first state to the second state, the second state to the third state, and the third state to the fourth state may produce tactile feedback via the interface member. In embodiments, the tactile feedback may be created by different angles of different portions of the slot cam.

In yet another aspect, the present disclosure relates to a method. The method may include placing an air input channel of a valve well in fluid communication with an atmospheric channel based on operation of a valve interface mechanism to a first state, the valve set comprising a primary control valve, an air input valve, and an atmospheric valve, wherein the primary control valve comprises the air input valve. The method may include placing the air input channel in fluid communication with an air output channel of the valve well based on operation of the valve interface mechanism to a second state. The method may include placing the water input channel in fluid communication with a water output channel of the valve well based on operation of the valve interface mechanism to a third state. The method may include placing the water input channel in fluid communication with the balloon channel of the valve well based on operation of the valve interface mechanism to a fourth state. In some embodiments, the method may include rotating an interface member in a first direction to operate the user interface mechanism to the second state and rotating the interface member in a second direction to operate the user interface mechanism to the third state and/or fourth state. In many embodiments, the method may include rotating the interface member adjust one or more valves in an air/water valve set via a cam. In several embodiments, the method may include operating one or more of a lever, a rocker switch, and an interface member to adjust between one or more of the first state, the second state, the third state, and the fourth state.

In still another aspect, the present disclosure relates to a method. The method may include configuring a valve set to place an air input channel of a valve well in fluid communication with an atmospheric channel based on operation of an interface member to a first state. The method may include configuring the valve set to place the air input channel in fluid communication with an air output channel of the valve well based on operation of the interface member to a second state. The method may include configuring the valve set to place the water input channel in fluid communication with a water output channel of the valve well based on operation of the interface member to a third state. The method may include configuring the valve set to place the water input channel in fluid communication with the balloon channel of the valve well based on operation of the interface member to a fourth state. In various embodiments, the method may comprise rotating the interface member in a first direction to operate the interface member to the third state and rotating the interface member in a second direction to operate the interface member to the fourth state. In some embodiments, the method may include translating the rotation of the interface member into a linear motion of one or more valves in the valve set via a cam. In several embodiments, the method may include translating the rotation of the interface member into a linear motion of one or more valves in the valve set via a slot cam.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 includes a block diagram of an exemplary suction valve assembly, according to one or more embodiments described herein.

FIG. 2 includes a block diagram of an exemplary air/water (AW) valve assembly, according to one or more embodiments described herein.

DETAILED DESCRIPTION

Figure 3A:
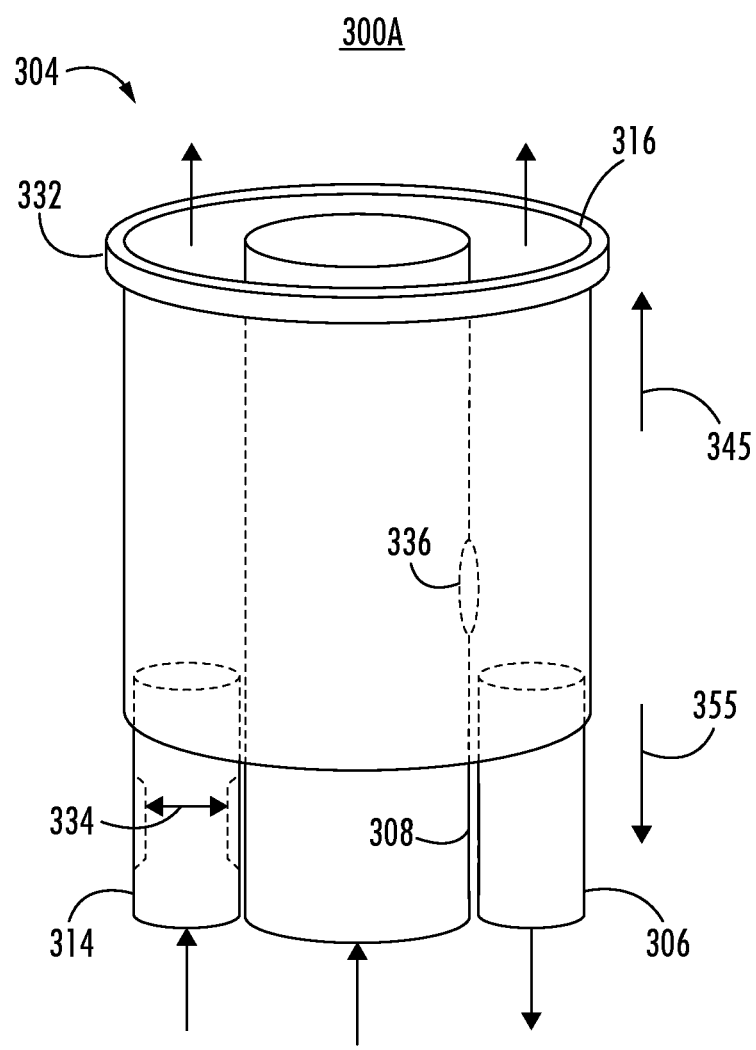
FIGS. 3A-3D illustrate various aspects of an exemplary suction valve well, according to one or more embodiments described herein.

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable. These and other embodiments are described and claimed.

Some challenges when controlling the flow of fluids through endoscopes include unreliable valves prone to failure. For example, many valves and valve interface mechanisms are fragile and likely to leak. These issues can be compounded when the components are designed, constructed, and/or assembled economically to facilitate disposal after a single use. Alternatively, these issues can be compounded when reusable components are worn down from multiple use/cleaning cycles. Adding further complexity, user interface mechanisms may be confusing to operate and require a steep learning curve. For instance, delicate and nonintuitive movements may be required to accurately control fluid flows. Further, little or no feedback may be provided to indicate how a set of valves is arranged. For example, an operator may not be able to easily discern via a user interface mechanism whether the set of valves is arranged to provide suction to a working channel or provide suction to a balloon channel. These and other factors may result in devices, systems, and methods for controlling the flow of fluids through endoscopes that are difficult to use, inaccurate, inefficient, and unreliable, resulting in limited applicability and/or uncertain outcomes. Such limitations can drastically reduce the dependability, ergonomics, and intuitiveness of flow control in endoscopes and procedures performed therewith, contributing to reduced usability, adverse outcomes, excess fatigue, and lost revenues.

Various embodiments described herein include one or more components of a valve assembly, such as valves and/or valve interface mechanisms, that provide reliable and intuitive control of fluid flow through endoscopes. In several embodiments, the components may provide reliable operation while providing sufficient value to be disposable (e.g., single-use). In many embodiments, the components may provide accurate and intuitive interfaces to improve operator experience. For example, embodiments may utilize one or more of up-and-down, forward-and-back, side-to-side, and rotational interfaces to provide ergonomic and intuitive control of fluid flows through endoscopes. Some such embodiments may include one or more interface members, such as push/pull switches, bellows, rotational switches, knobs, buttons, and toggle switches. In many embodiments, one or more of the components may provide/enable tactile feedback. For example, one or more components of the valve interface mechanism may provide tactile or haptic feedback to indicate how a set of valves is arranged (e.g., arranged to permit/block flows between various channels). In some examples, the force to operate a user interface mechanism may vary to indicate transitions between valve states. In various embodiments, tactile feedback may be produced as a result of different components of a valve assembly coming into contact, such as due to received input.

In various embodiments, one or more of the components may be designed to simplify manufacturability. For instance, the location of one or more biasing members may simplify component assembly. In these and other ways, components/techniques described here may improve operator experience, decrease learning curves, improve reliability, and/or decrease manufacturing complexity via realization of more efficient and valuable devices, systems, and methods for controlling the flow of fluids in endoscopic systems. In many embodiments, one or more of the advantageous features may result in several technical effects and advantages over conventional technology, including increased capabilities and improved adaptability.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to specific medical devices and systems (e.g., an endoscope), it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures, Endoscopic Retrograde Cholangio-Pancreatography (ERCP) procedures, and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional/operator when introducing a device into a patient, while the term "proximal" refers to the end closest to the medical professional when introducing a device into a patient.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may provide reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked, and/or the flow of water may be controlled from water input channel 208 to one of water output channel 212, the balloon channel 214, or blocked.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to provide medium to facilitate transmission of sound waves and capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214. In other embodiments, one or more of the components of the valve assembly for AW and/or suction may be implemented in configurations that do not require or include a balloon, such as video capable scope with ultrasound functionality.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a lever, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa, without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve well block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Figure 3B:
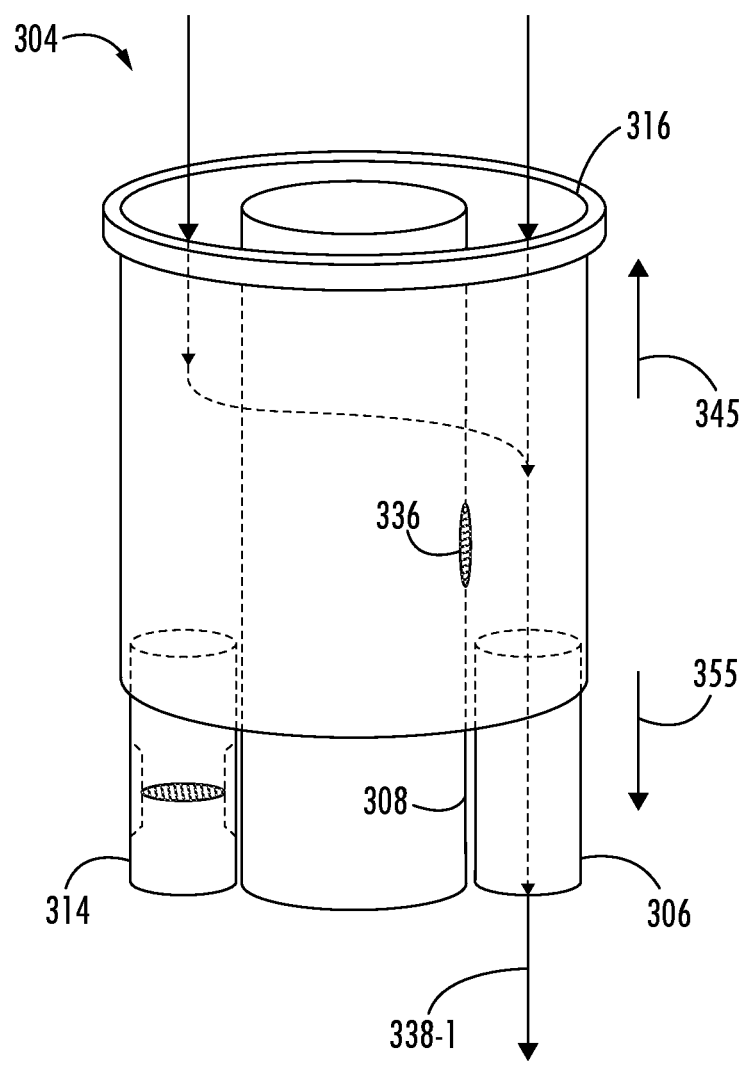

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. For example, suction channel 306 may be an input in the handle of a medical scope that is connected to a vacuum system, such as for a hospital, home, and/or mobile device.

Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Figure 3C:
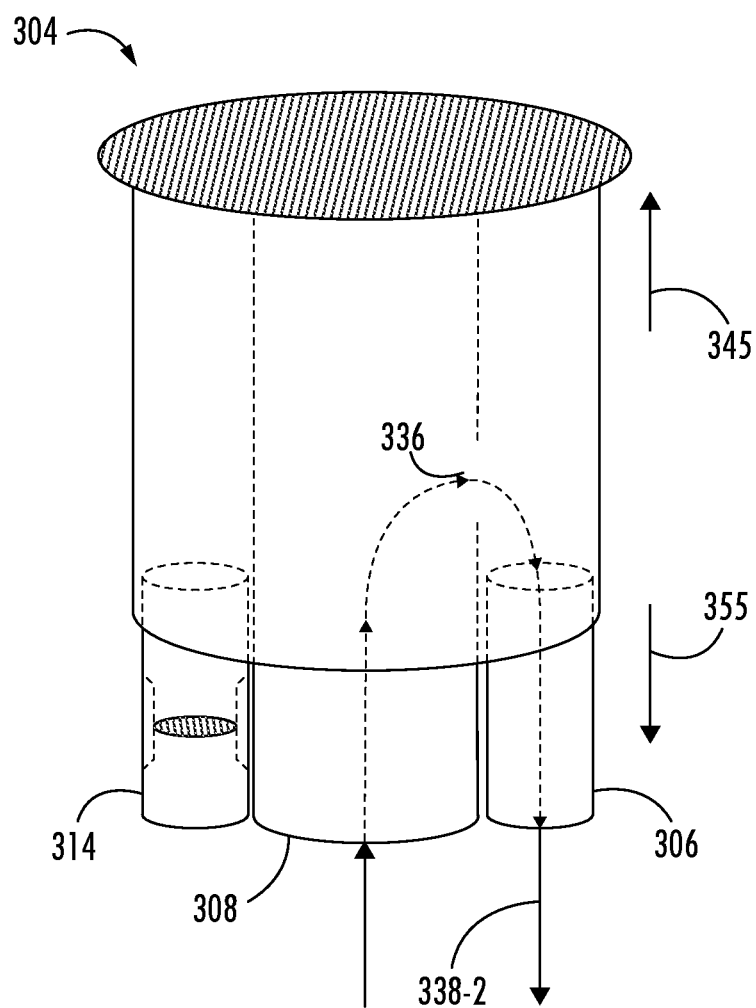

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Figure 3D:
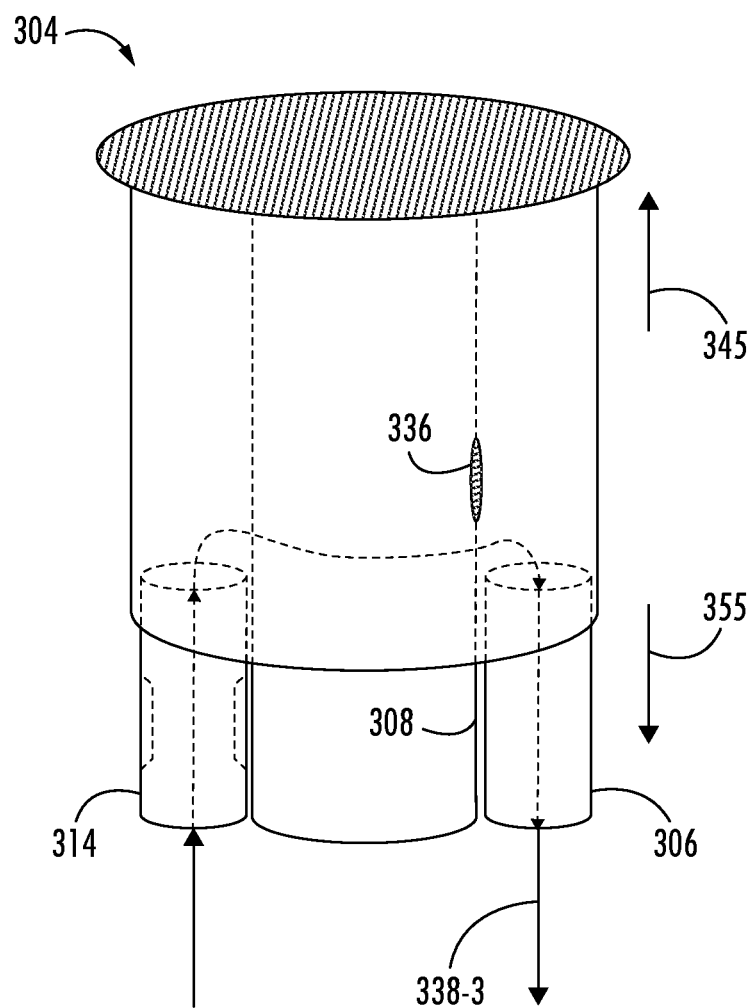

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Figure 4A:
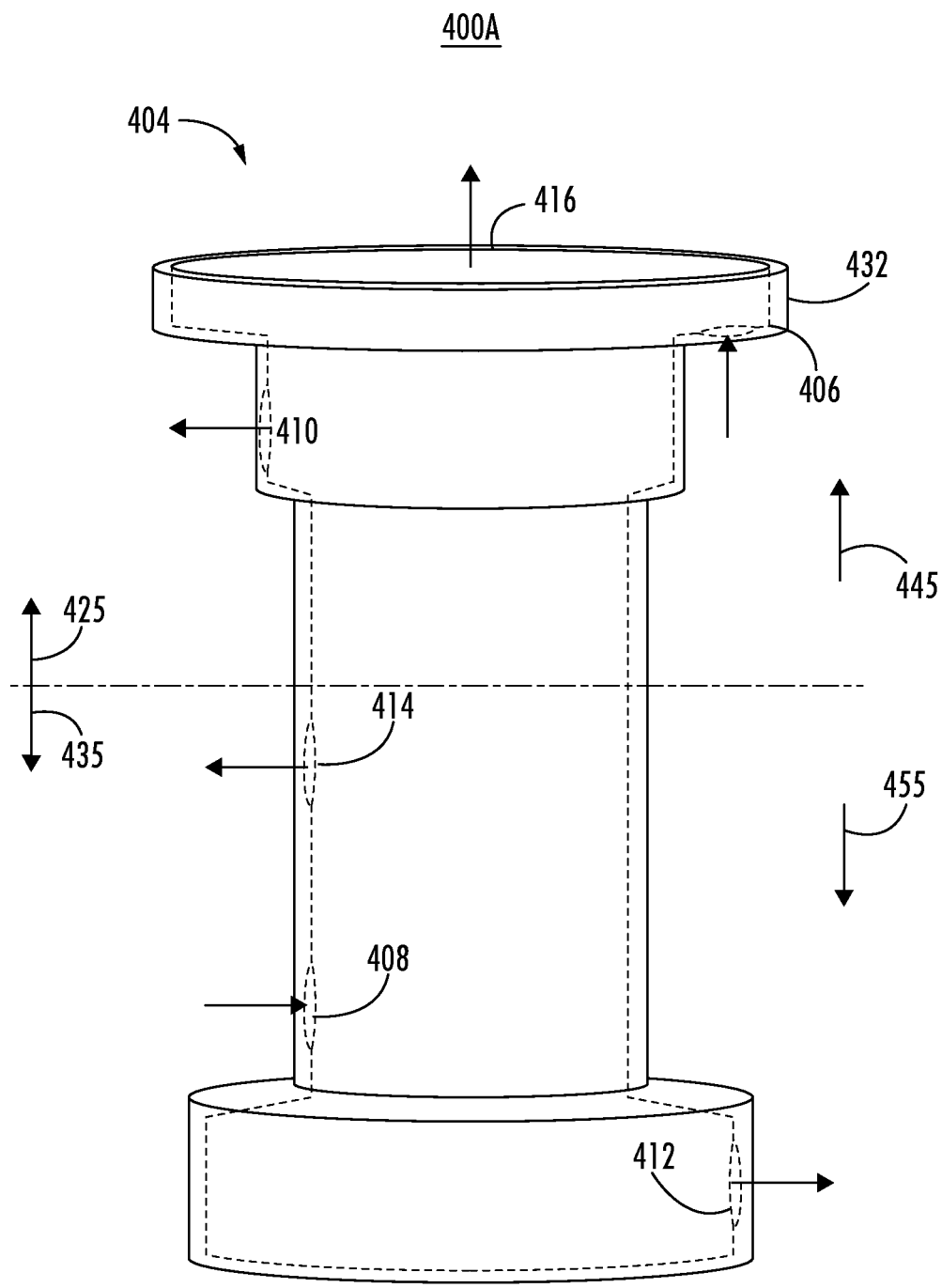
FIGS. 4A-4E illustrate various aspects of an exemplary AW valve well, according to one or more embodiments described herein.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Figure 4B:
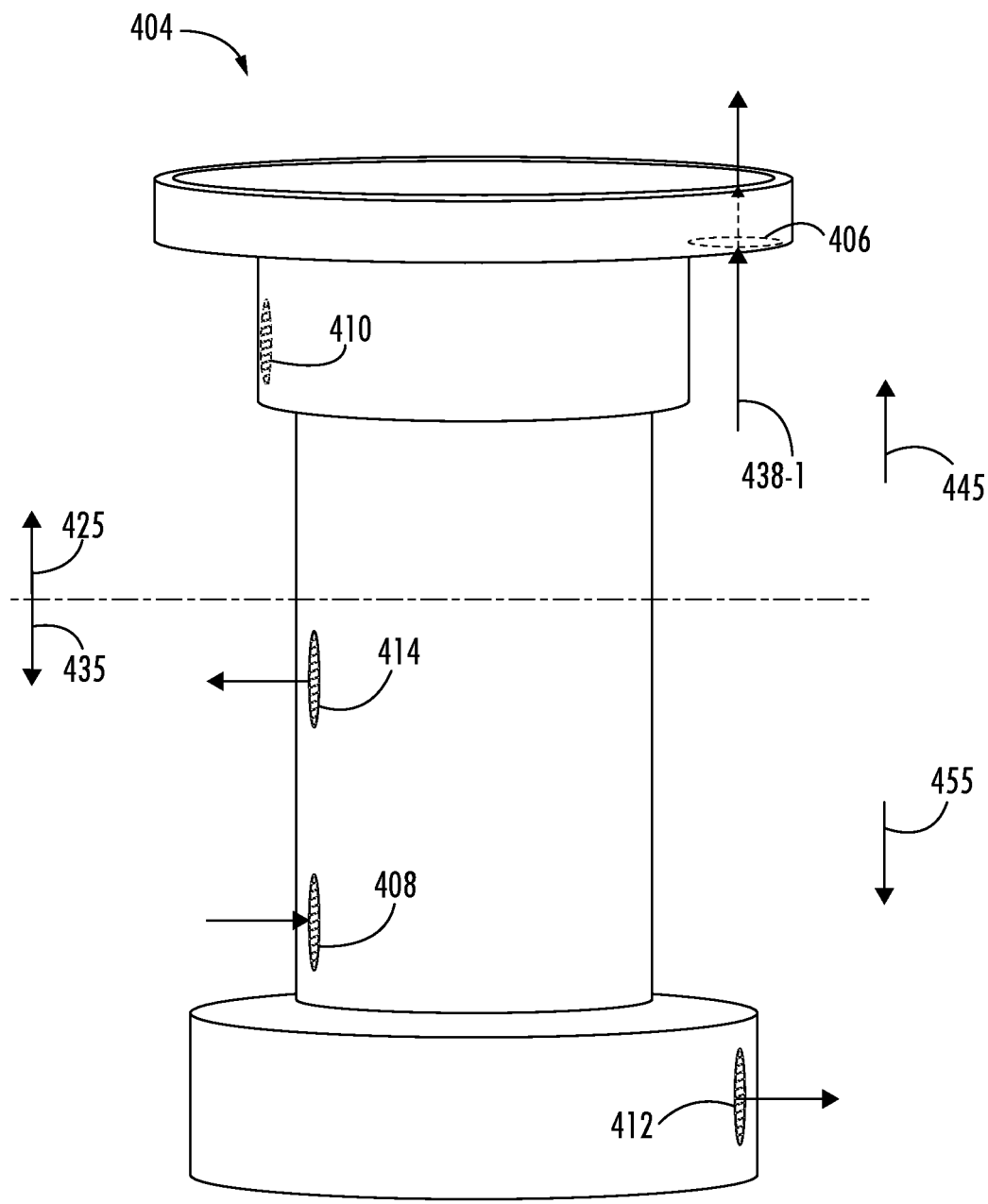

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Figure 4C:
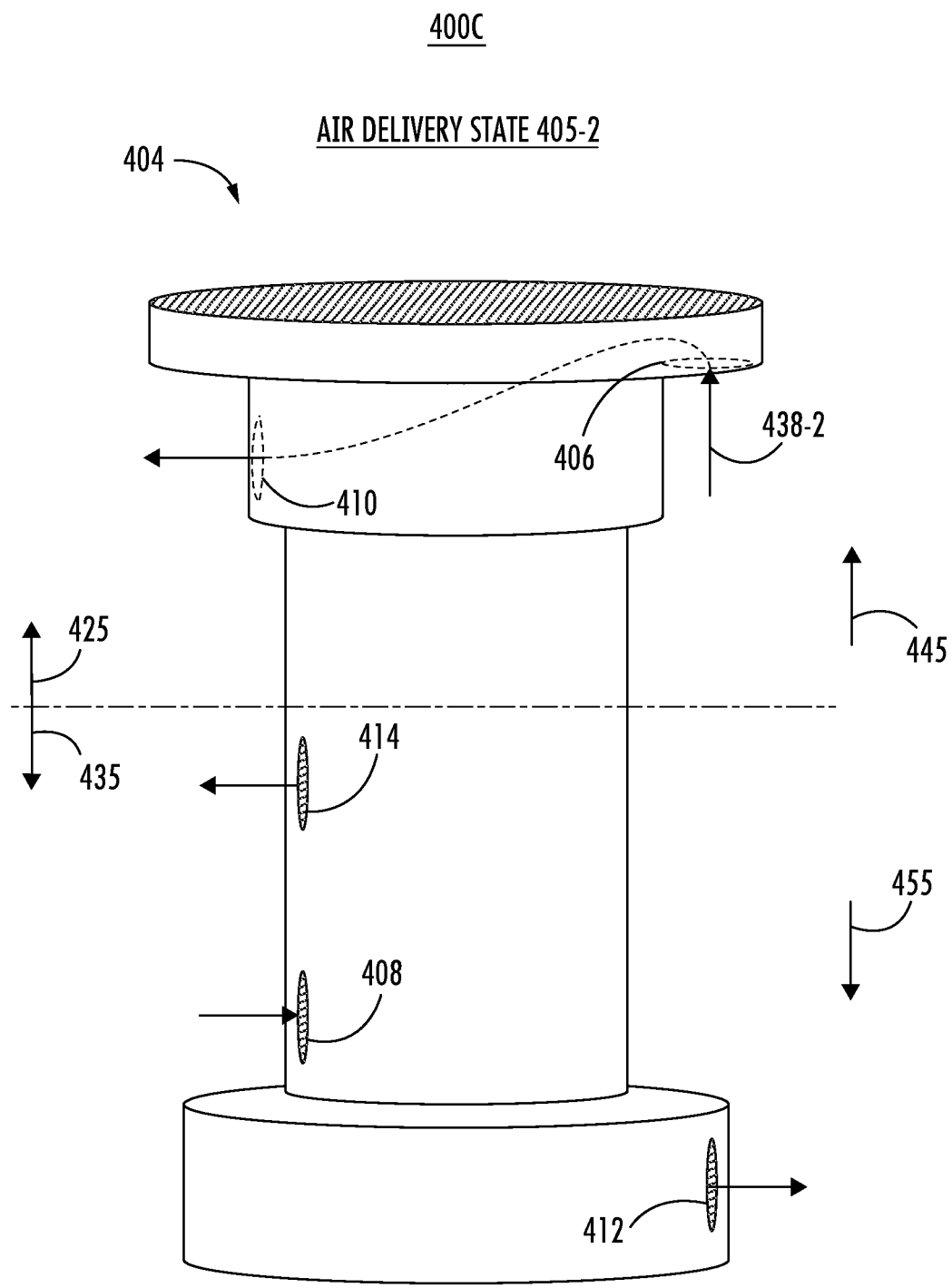

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Figure 4D:
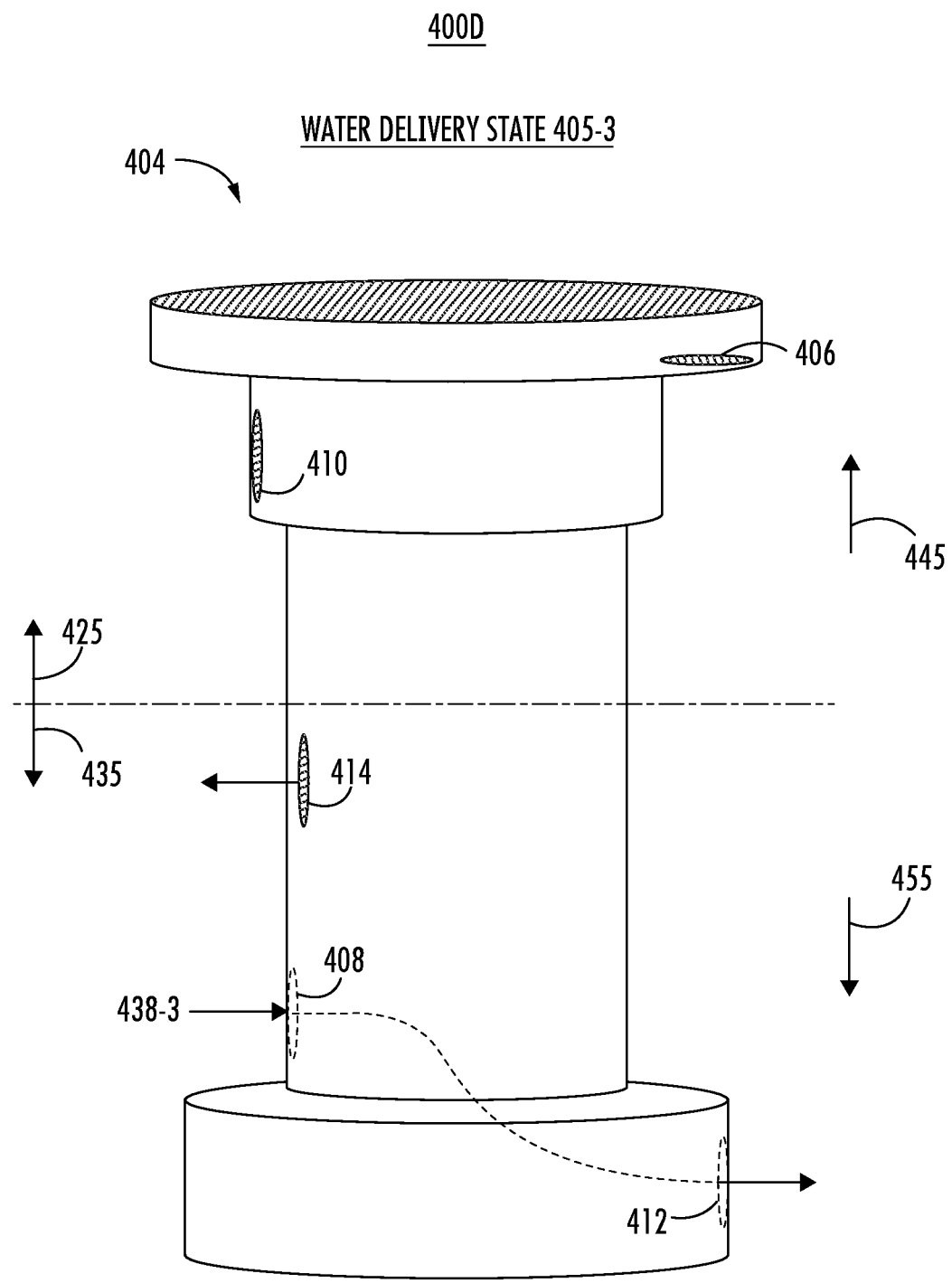

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Figure 4E:
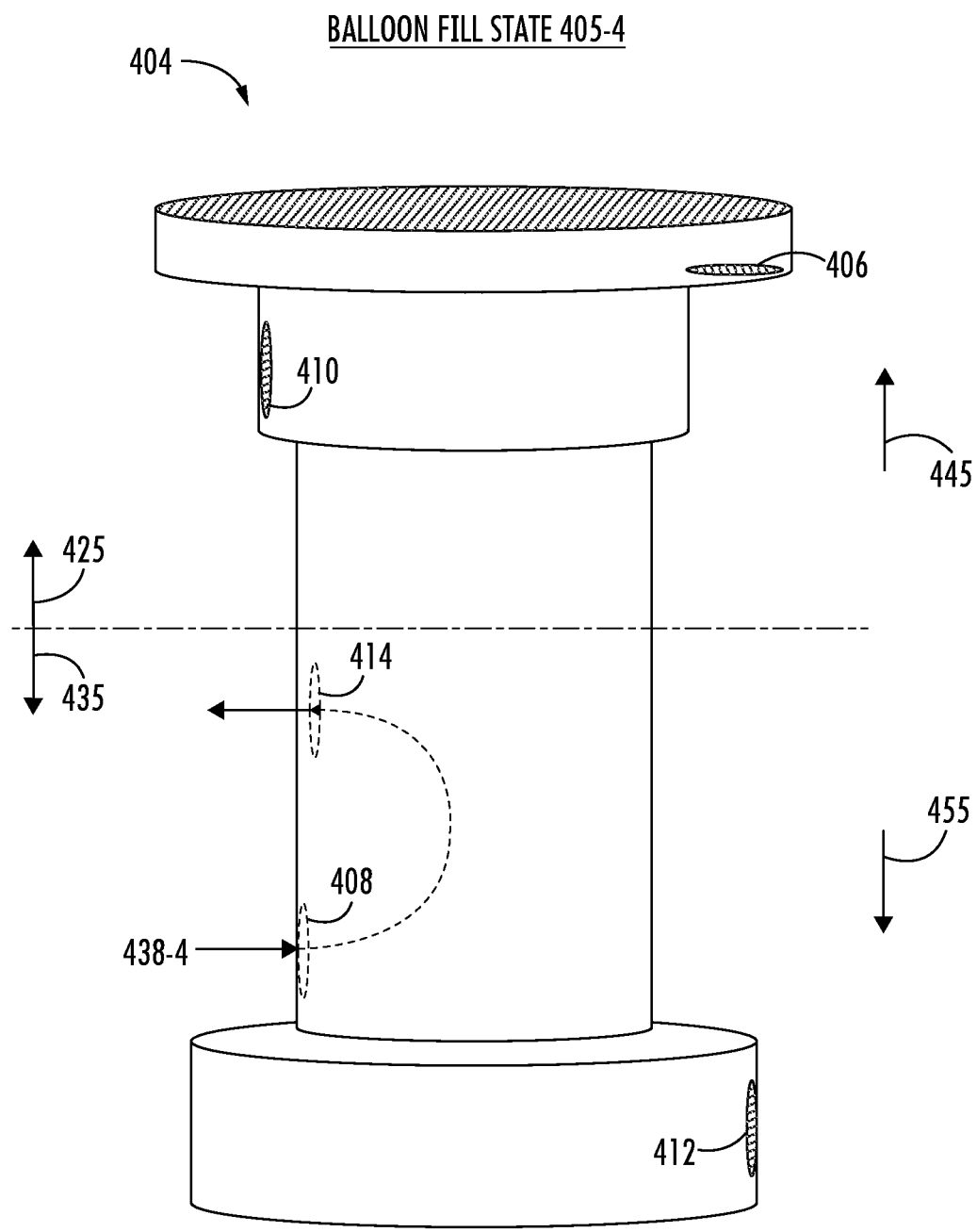

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Figure 5:
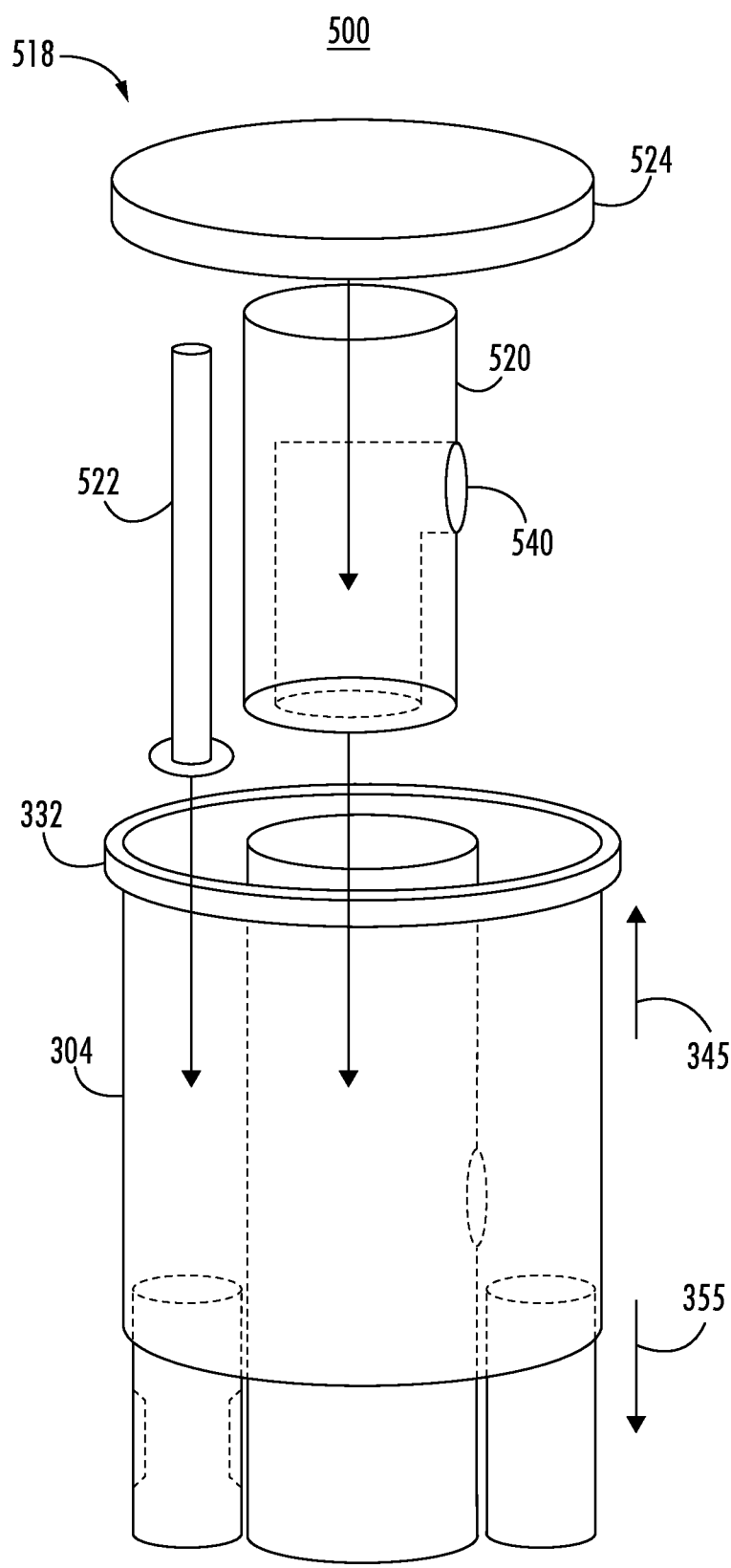
FIG. 5 illustrates an exemplary suction valve set, according to one or more embodiments described herein.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel 314 of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Figure 6A:
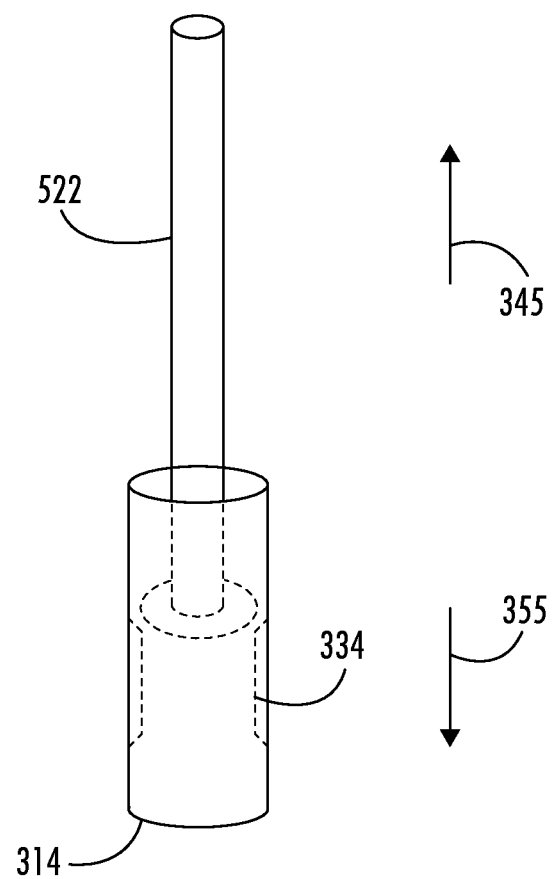
FIGS. 6A-8C illustrate various aspects of exemplary valves in suction valve sets, according to one or more embodiments described herein.
Figure 6B:
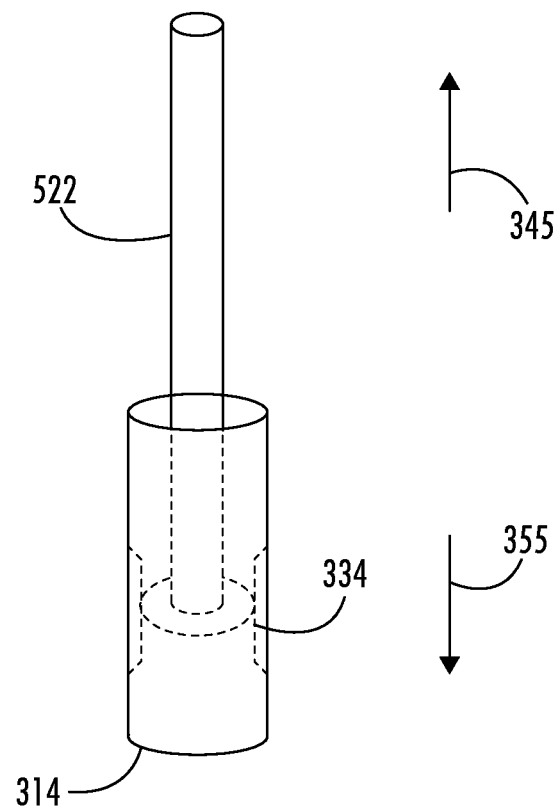

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Figure 7A:
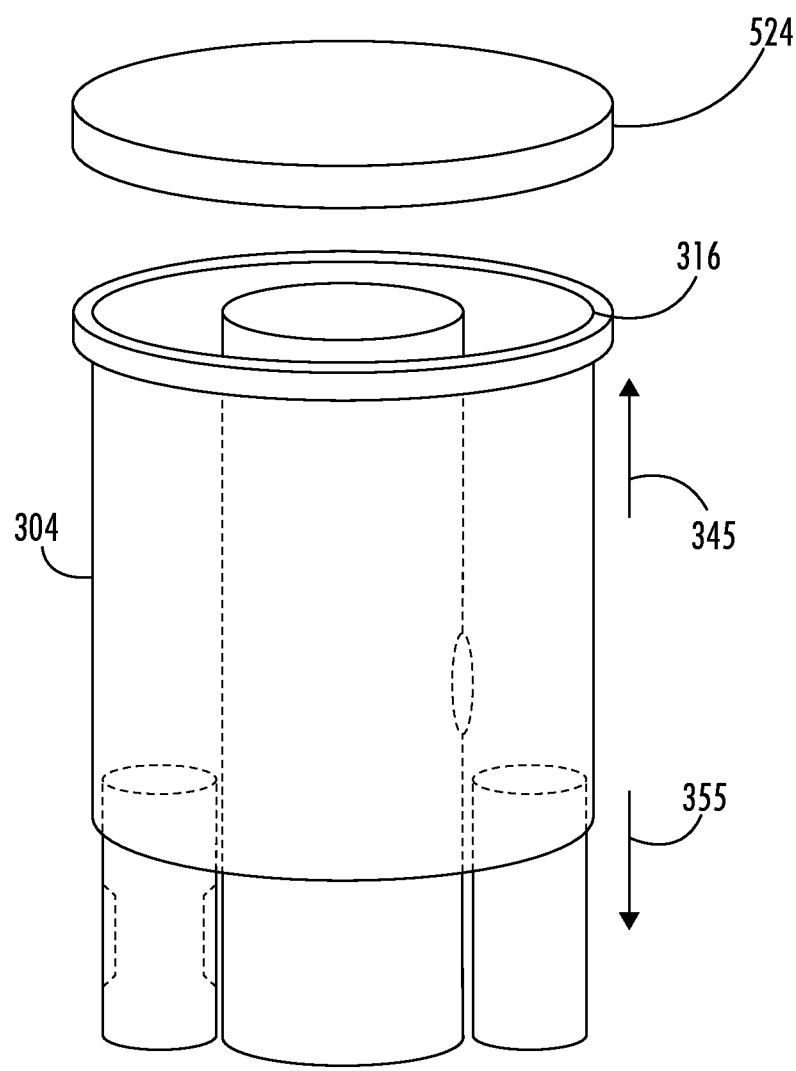
Figure 7B:
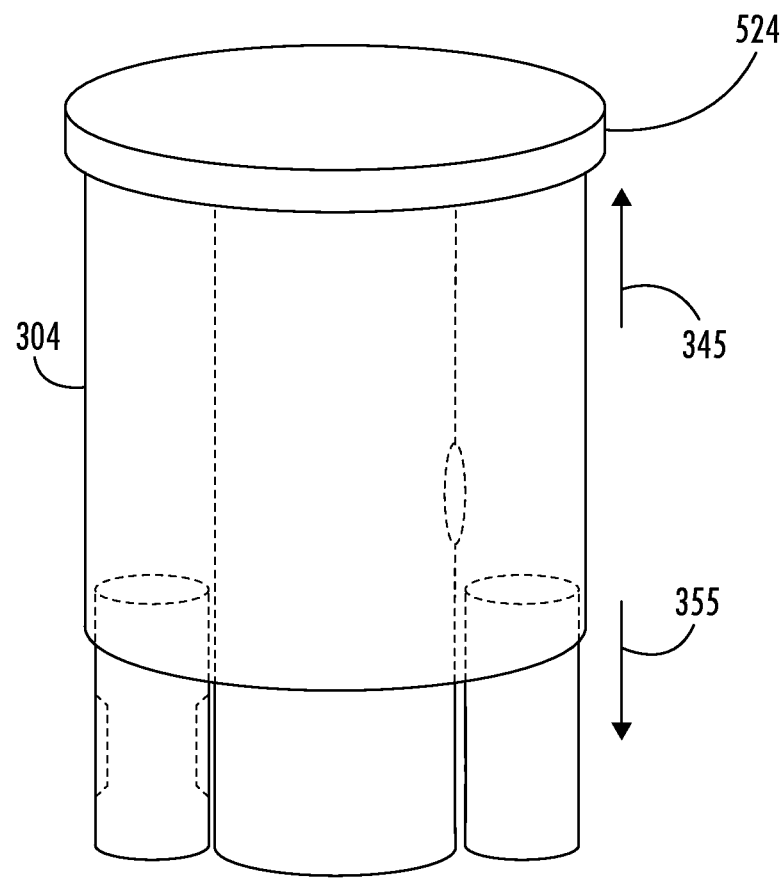

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Figure 8A:
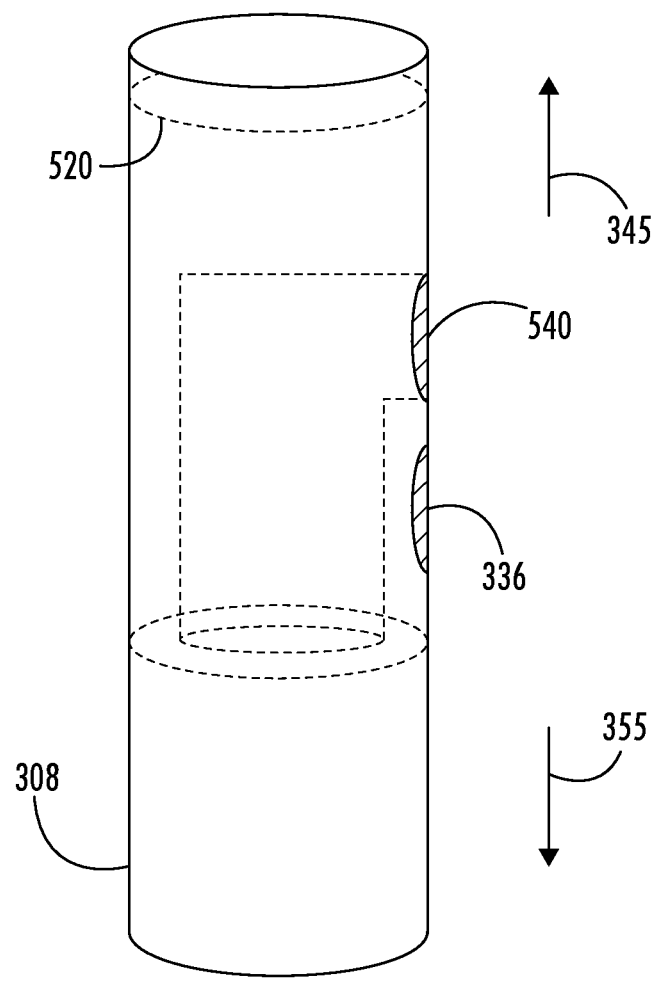
Figure 8B:
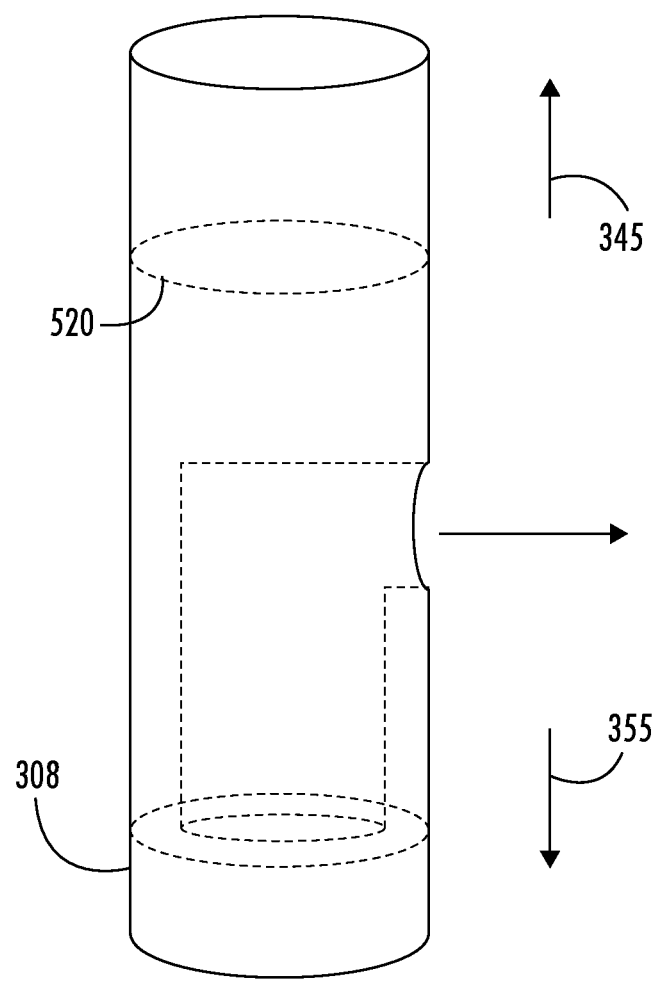
Figure 8C:
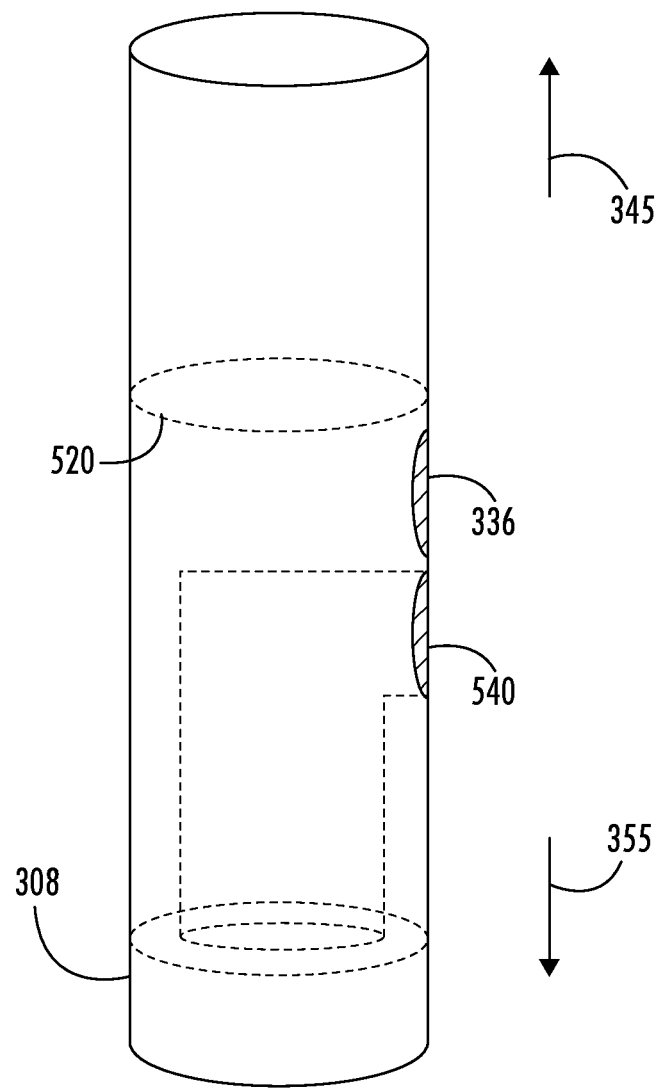

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit suction flow through working channel 308. For example, the flow may enter through the bottom of the working channel valve 520 and exit through the well radial hole 336. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel radial hole 440 is below well radial hole 336.

Figure 9:
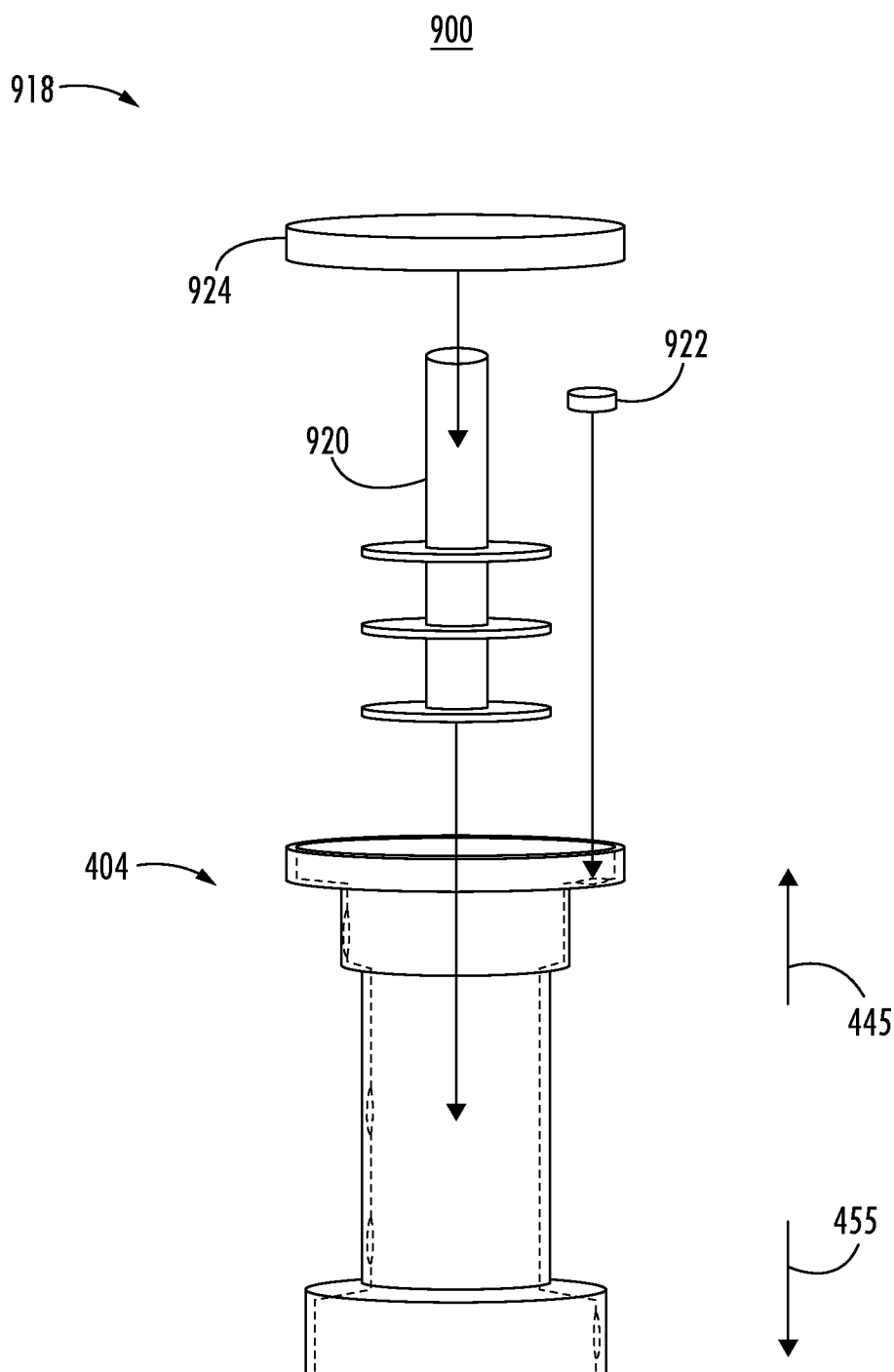
FIG. 9 illustrates an exemplary AW valve set, according to one or more embodiments described herein.

Referring to FIG. 9, environment 900 illustrates AW valve set 918 in conjunction with AW valve well 404. AW valve set 918 may include primary control valve 920, air input valve 922, and atmospheric valve 924. In several embodiments, the primary control valve 920 may be inserted into the AW valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

Figure 10A:
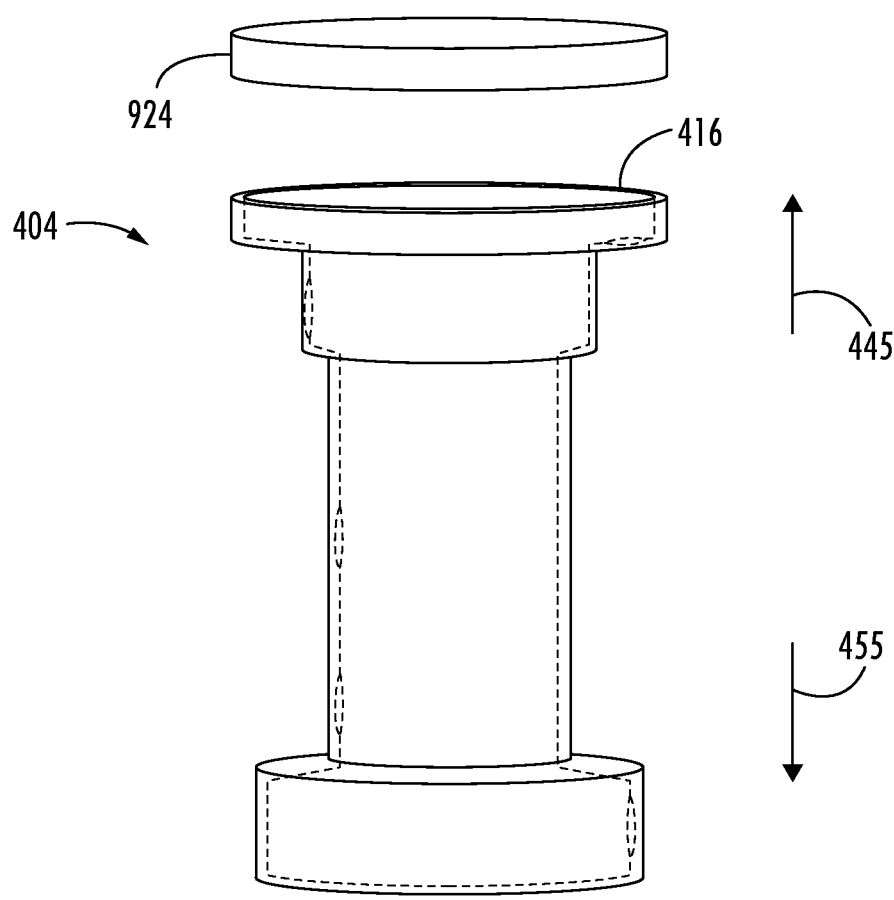
FIGS. 10A-12C illustrate various aspects of exemplary valves in AW valve sets, according to one or more embodiments described herein.
Figure 10B:
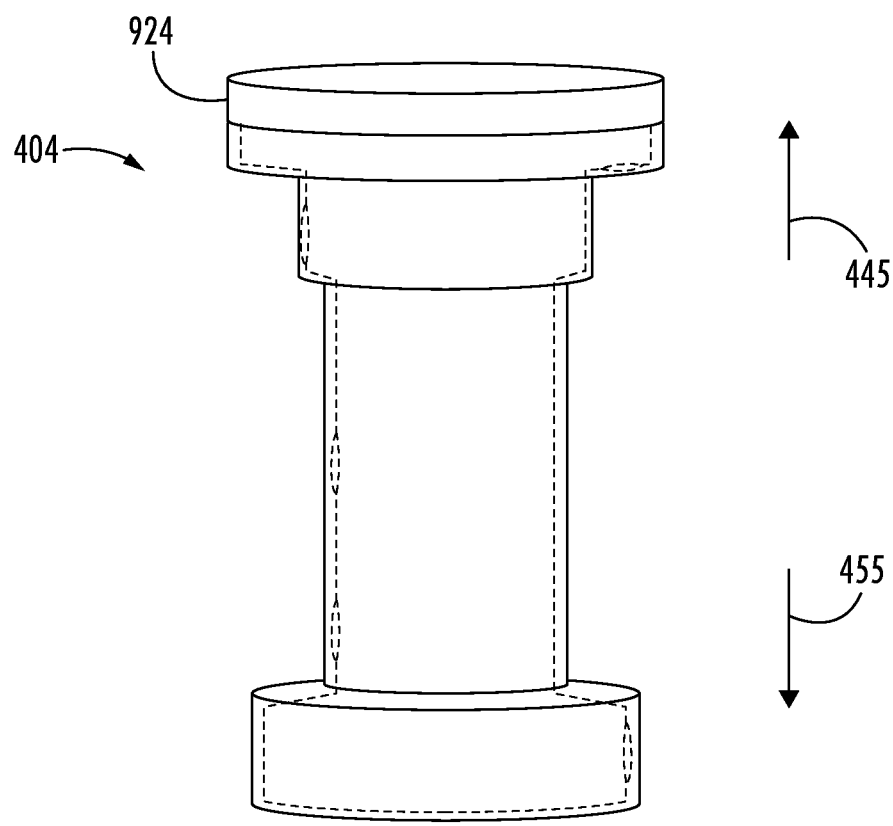

Referring to FIG. 10A, environment 1000A illustrates an atmospheric valve open state. In the atmospheric valve open state, the atmospheric valve 924 may allow flow through the atmospheric channel of AW valve well 404. Referring to FIG. 10B, environment 1000B illustrates an atmospheric valve sealed state 1015-2. In the atmospheric valve sealed state 1015-2, the atmospheric valve 924 may prevent flow through atmospheric channel of AW valve well 404. As will be discussed in more detail below, in operation, fluid communication with the atmosphere may be provided through a passage/channel in, or created by, one or more components (e.g., primary control valve 920). Further, one or more components may be used to seal portions of the atmospheric channel 316 to facilitate control of fluid communication with the atmosphere by atmospheric valve 924. In some embodiments, atmospheric valve 924 may include a plurality of components configured to control fluid communication with the atmosphere.

Figure 11A:
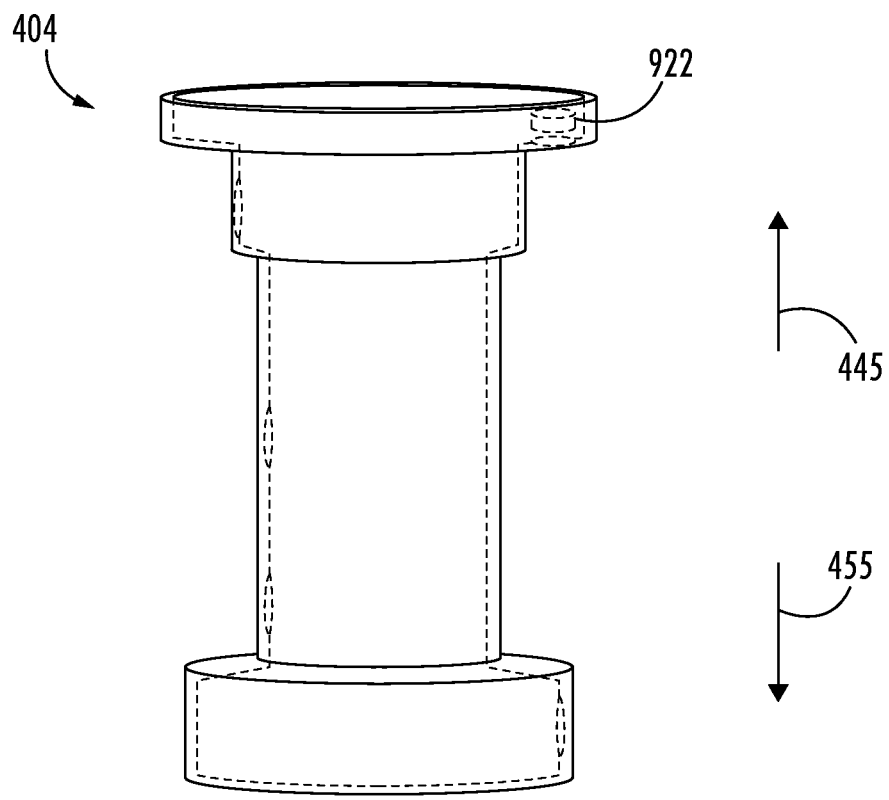
Figure 11B:
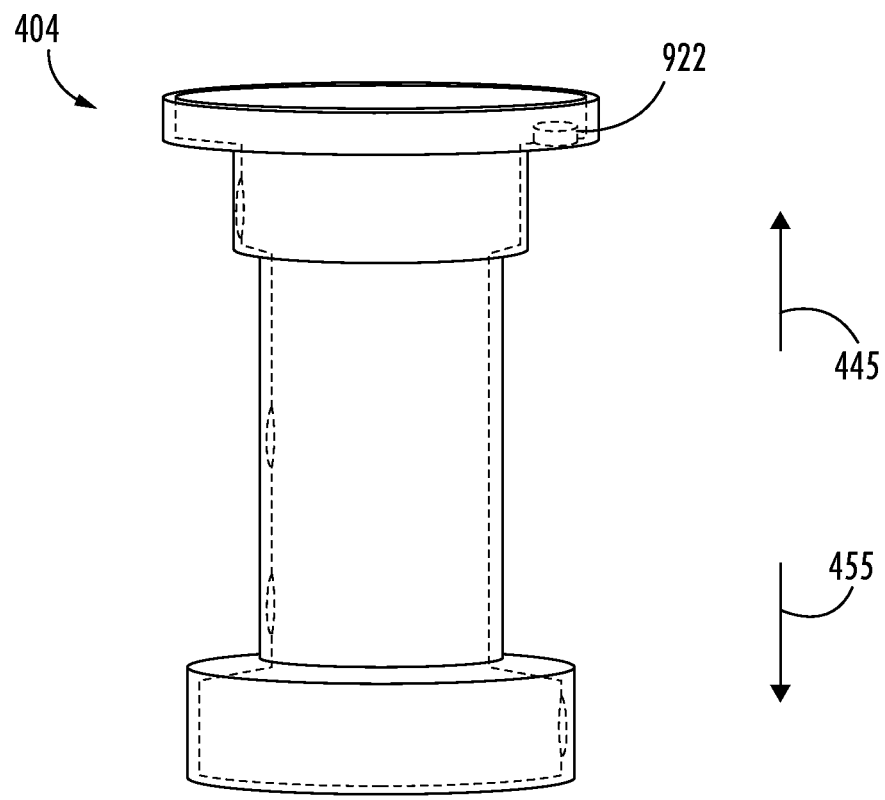

Referring to FIG. 11A, environment 1100A illustrates an air input valve open state 1115-1. In the air input valve open state 1115-1, the air input valve 522 may allow flow through the air input channel of AW valve well 404. Referring to FIG. 11B, environment 1100B illustrates an air input valve sealed state 1115-2. In the air input valve sealed state 1115-2, the air input valve 922 may prevent flow through the air input channel of AW valve well 404. In some embodiments, sealing the air input channel may cause a fluid source (e.g., water reservoir) to be pressurized, thereby enabling/causing fluid to flow into the AW valve well 404 via water input channel 408.

Figure 12A:
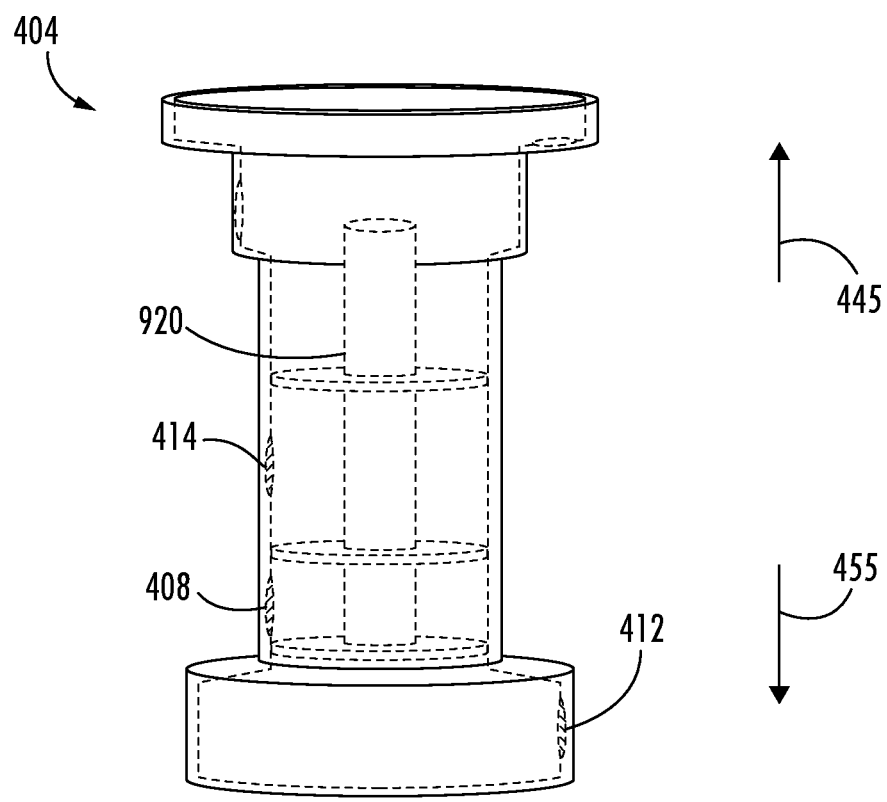
Figure 12B:
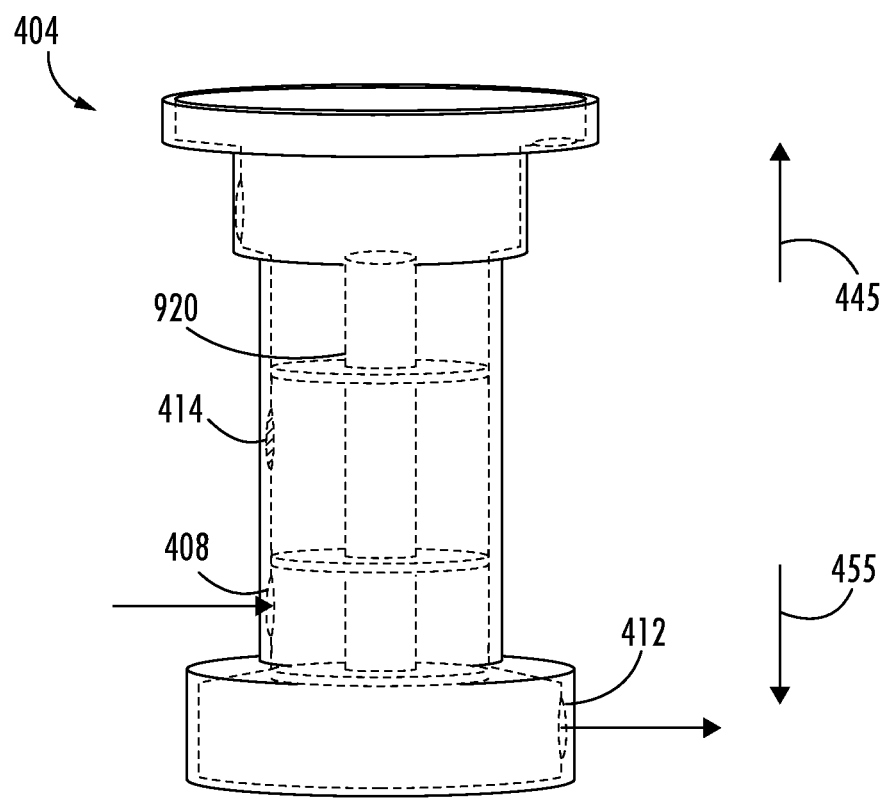
Figure 12C:
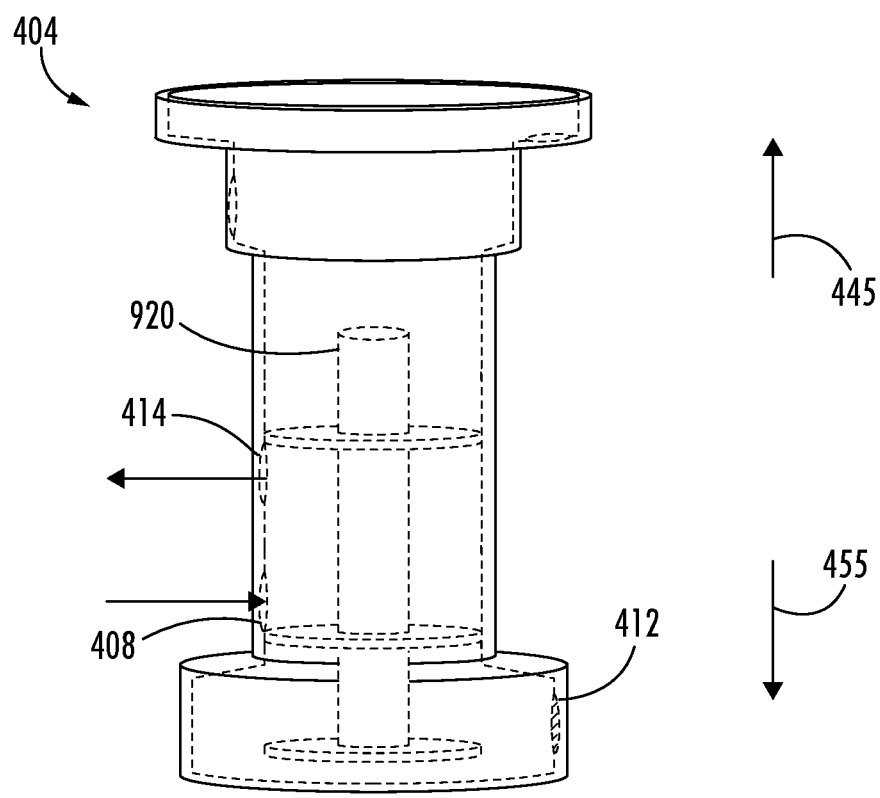
Figure 13:
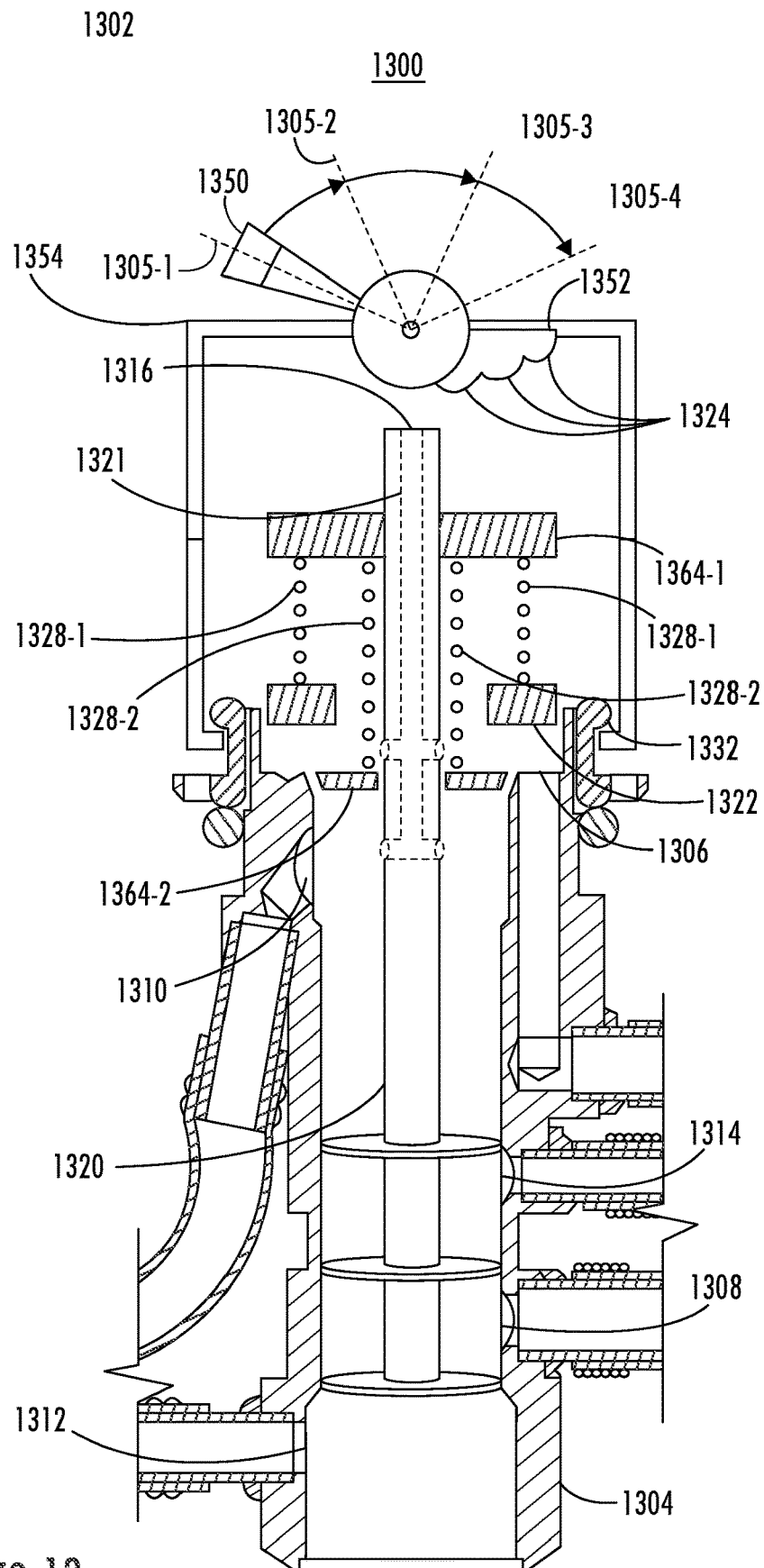
FIG. 13 illustrates an exemplary AW valve assembly, according to one or more embodiments described herein.

Referring to FIG. 12A, environment 1200A illustrates a primary valve sealed state 1215-1. In the primary valve sealed state 1215-1, the primary control valve 920 may prevent flow through one or more of the balloon channel 414, water input channel 408, and water output channel 412. Referring to FIG. 12B, environment 1200B illustrates a primary valve water output state 1215-2. In the primary valve water output state 1215-2, the primary control valve 920 may be positioned to block flow through balloon channel 414 and permit flow from water input channel 408 to water output channel 412. In various embodiments, primary control valve 920 may utilize changes in diameter in AW valve well 404 to control flow. Referring to FIG. 12C, environment 1200C illustrates a primary valve balloon fill state 1215-3. In the primary valve balloon fill state 1215-3, the primary control valve 920 may be positioned to block flow through water output channel 412 and permit flow from water input channel 408 to balloon channel 414. In various embodiments, one or more features of primary control valve 920 may operate as valves for multiple channels. In some embodiments, one or more features of primary control valve 920 may comprise one or more channels, or one or more portions thereof. For example, primary control valve 920 may comprise atmospheric channel 416. FIG. 13 illustrates an exemplary AW valve assembly 1302 in environment 1300, according to one or more embodiments described herein. In many embodiments, a cross section of one or more portions of AW valve assembly 1302 may be illustrated in environment 1300. In some embodiments, one or more components of FIG. 13 may be the same or similar to one or more other components described herein. AW valve assembly 1302 includes an AW valve well 1304, an AW valve set, and a valve interface mechanism. The AW valve well 1304 includes air input channel 1306, water input channel 1308, air output channel 1310, water output channel 1312, balloon channel 1314, and lip 1332. The AW valve set may include primary control valve 1320 with interior channel 1321 and atmospheric channel 1316, air input valve 1322, and atmospheric valve 1324. In the illustrated embodiment, the air input valve 1322 and the atmospheric valve 1324 may include, or be included in, one or more portions of the valve interface mechanism. The valve interface mechanism includes biasing members 1328-1, 1328-2, toggle 1350, cam 1352 with atmospheric valve 1324, housing 1354, and linkages 1364-1, 1364-2. In one or more embodiments described herein, toggle 1350 may be moved to control the flow of fluid through AW valve assembly 1302, such as by switching between an air escape state 1305-1, an air delivery state 1305-2, a water delivery state 1305-3, and a balloon fill state 1305-4. Embodiments are not limited in this context.

In some embodiments, the linkage 1364-1 may be attached to, or included in, primary control valve 1320. In various embodiments, air input valve 1322 may be coupled to linkage 1364-1 via biasing member 1328-1. In many embodiments, linkage 1364-2 may seat in the AW valve well 1304 to enable biasing member 1328-2 to push against linkage 1364-1 and bias primary control valve 1320 toward the top. In several embodiments, primary control valve 1320 may be able to slide up and down through linkage 1364-2. In the illustrated embodiment, housing 1354 may couple to the AW valve well 1304 via lip 1332. The housing 1354 may provide a rigid mounting point for one or more components of AW valve assembly 1302, such as for toggle 1350 and cam 1352 to rotatably couple to.

In many embodiments, cam 1352 may enable motion of toggle 1350 to be translated into linear motion of primary control valve 1320. In various embodiments, cam 1352 may include a profile with one or more steps, such as to seal atmospheric channel 1316 and/or move primary control valve 1320 toward the bottom. As shown in the illustrated embodiment, cam 1352 may include three steps or levels with a first step corresponding to the air delivery state 1305-2, a second step corresponding to the water delivery state 1305-3, and a third step corresponding to the balloon fill state 1305-4. Accordingly, articulating toggle 1350 between different positions may cause cam 1352 to contact and/or move primary control valve 1320 to switch between the air escape state 1305-1, the air delivery state 1305-2, the water delivery state 1305-3, and the balloon fill state 1305-4. In several embodiments, a spring may be coupled to toggle 1350 to bias the toggle 1350, and thereby the primary control valve 1320, into a specific position or state.

Referring to air escape state 1305-1, the cam 1352 may be positioned out of contact with the primary control valve 1320 to enable fluid from air input valve 1322 through the interior channel 1321 and escape to atmosphere through the top of the primary control valve 1320 via atmospheric channel 1316. With cam 1352 positioned out of contact with the primary control valve 1320, biasing member 1328-2 may force primary control valve 1320 toward the top of the AW valve assembly 1302. Further, biasing member 1328-1 may ensure that air input valve 1322 is in an open state due to biasing member 1328-2 forcing primary control valve 1320 toward the top of the AW valve assembly 1302.

Referring to air delivery state 1305-2, the first step of cam 1352 may be positioned in contact with the primary control valve 1320 such that the first step of the cam 1352 acts as atmospheric valve 1324 and seals atmospheric channel 1316. In the air delivery state 1305-2, fluid may flow from the air input channel 1306 to the air output channel 1310 via interior channel 1321. With the first step of cam 1352 positioned in contact with the primary control valve 1320, biasing member 1328-2 may force primary control valve 1320 toward the top of the AW valve assembly 1302 to facilitate sealing between the atmospheric channel 1316 and the first step of the cam 1352. Further, the first step of cam 1352 may only slightly compress biasing member 1328-2 and slightly force linkage 1364-1 downward such that biasing member 1328-1 is still able to ensure that air input valve 1322 is in an open state due to biasing member 1328-2 forcing primary control valve 1320 toward the top of the AW valve assembly 1302.

Referring to water delivery state 1305-3, the second step of cam 1352 may be positioned in contact with the primary control valve 1320 such that the second step of the cam 1352 acts as atmospheric valve 1324 and seals atmospheric channel 1316. Additionally, positioning the second step of cam 1352 in contact with the primary control valve 1320 may force the primary control valve 1320 toward the bottom, causing air input valve 1322 to seal against air input channel 1306 and placing water input channel 1308 in fluid communication with water output channel 1312. In the water delivery state 1305-3, fluid flow from the air input channel 1306 may be blocked by air input valve 1322 and fluid may flow from the water input channel 1308 to the water output channel 1312. With the second step of cam 1352 positioned in contact with the primary control valve 1320, biasing member 1328-2 may force primary control valve 1320 toward the top of the AW valve assembly 1302 to facilitate sealing between the atmospheric channel 1316 and the second step of the cam 1352. Further, the second step of cam 1352 may compress biasing member 1328-2 and force linkage 1364-1 downward such that biasing member 1328-1 forces air input valve 1322 downward to seal air input channel 1306.

Referring to balloon fill state 1305-4, the third step of cam 1352 may be positioned in contact with the primary control valve 1320 such that the third step of the cam 1352 acts as atmospheric valve 1324 and seals atmospheric channel 1316. Additionally, positioning the third step of cam 1352 in contact with the primary control valve 1320 may force the primary control valve 1320 toward the bottom, causing air input valve 1322 to seal against air input channel 1306 and placing water input channel 1308 in fluid communication with balloon channel 1314. In the balloon fill state 1305-4, fluid flow from the air input channel 1306 may be blocked by air input valve 1322 and fluid may flow from the water input channel 1308 to the balloon channel 1314. With the third step of cam 1352 positioned in contact with the primary control valve 1320, biasing member 1328-2 may force primary control valve 1320 toward the top of the AW valve assembly 1302 to facilitate sealing between the atmospheric channel 1316 and the third step of the cam 1352. Further, the third step of cam 1352 may compress biasing member 1328-2 and force linkage 1364-1 downward such that biasing member 1328-1 forces air input valve 1322 downward to seal air input channel 1306.

FIGS. 14A-14E illustrate various aspects of an exemplary AW valve assembly 1402 in environments 1400A-E, according to one or more embodiments described herein. In many embodiments, a cross section of one or more portions of AW valve assembly 1402 may be illustrated in environments 1400A-E. In some embodiments, one or more components of FIGS. 14A-14E may be the same or similar to one or more other components described herein. AW valve assembly 1402 includes an AW valve well 1404, an AW valve set, and a valve interface mechanism 1426. In the illustrated embodiment, AW valve well 1404 is be the same as AW valve well 1304. Accordingly, fewer components of AW valve well 1404 are labeled for simplicity. The AW valve set may include air input valve 1422 and primary control valve 1420 with interior channel 1421, atmospheric channel 1416, and radial air hole 1466. In the illustrated embodiment, the air input valve 1422 may include, or be included in, one or more portions of the primary control valve 1420 and/or the valve interface mechanism 1426. The valve interface mechanism 1426 includes housing 1454, knob 1456, interface 1458, slot cam 1460, cam pin 1462, and linkage 1464. In one or more embodiments described herein, knob 1456 may be rotated, such as via interface 1458, to control the flow of fluid through AW valve assembly 1402. Accordingly, in FIGS. 14A-14E, respectively, environment 1400B may illustrate one or more aspects of an air escape state, environment 1400C may illustrate one or more aspects of an air delivery state, environment 1400D may illustrate one or more aspects of a water delivery state, and environment 1400E may illustrate one or more aspects of a balloon fill state. Embodiments are not limited in this context.

Referring to environment 1400A, in some embodiments, the linkage 1464 may be attached to, or included in, primary control valve 1420. In various embodiments, air input valve 1422 may be attached to, or included in, primary control valve 1420. In many embodiments, linkage 1464 may be disposed within interior channel 1421. In other embodiments, interior channel 1421 may be disposed within linkage 1464. In the illustrated embodiment, housing 1454 may couple to the AW valve well 1404 via lip 1332. The housing 1454 may provide a rigid mounting point for one or more components of AW valve assembly 1402, such as for knob 1456 to rotatably couple to.

In many embodiments, knob 1456 may be rotated to control the position of the primary control valve 1420 in AW valve well 1404. In many such embodiments, rotating knob 1456 may cause the cam pin 1462 to follow the profile of the slot cam 1460 and force the primary control valve 1420 up or down, as will be described in more detail below with respect to environments 1400D, 1400E. In some embodiments, rotating knob 1456, such as via interface 1458, may cause block flow through one or more of atmospheric channel 1416, interior channel 1421, and radial air hole 1466. For instance, rotating knob 1456 may block fluid communication between radial air hole 1466 and atmospheric channel 1416. In some embodiments, radial air hole 1466 may include a plurality of holes provided access to interior channel 1421.

In several embodiments, a torsional spring may be coupled to knob 1456 to bias the knob 1456, and thereby the primary control valve 1420, into a specific position. In the illustrated embodiment, knob 1456 is biased such that cam pin 1462 is in a flat portion in the middle of slot cam 1460. However, in other embodiments, knob 1456 is biased such that cam pin 1462 is on one side or the other of slot cam 1460. Further, in other embodiments, slot cam 1460 may take on a variety of geometries. For instance, slot cam 1460 may include flat portions on each side. In another instance, slot cam 1460 may include additional angled sections, such as additional angled sections configured to further raise or lower primary control valve 1420, and/or close atmospheric channel 1416. In one or more embodiments, the geometry of the slot cam 1460 may provide tactile feedback. For example, the flat portions and/or different angles of sections may provide tactile feedback. An alternative slot cam geometry is included in environments 1400B, 1400C for illustrative purposes.

Figure 14A:
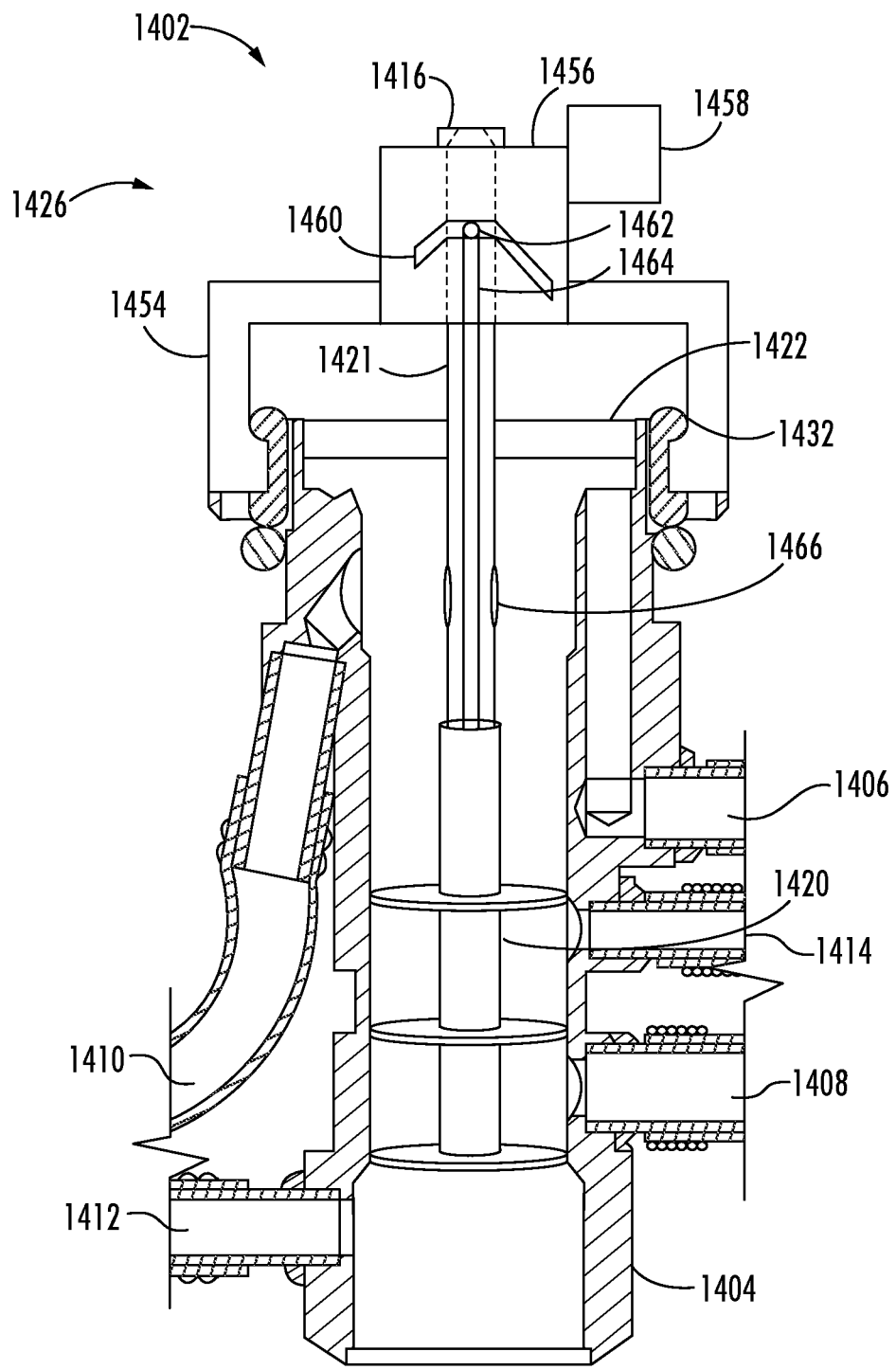
FIGS. 14A-14E illustrate various aspects of an exemplary AW valve assembly, according to one or more embodiments described herein.
Figure 14B:
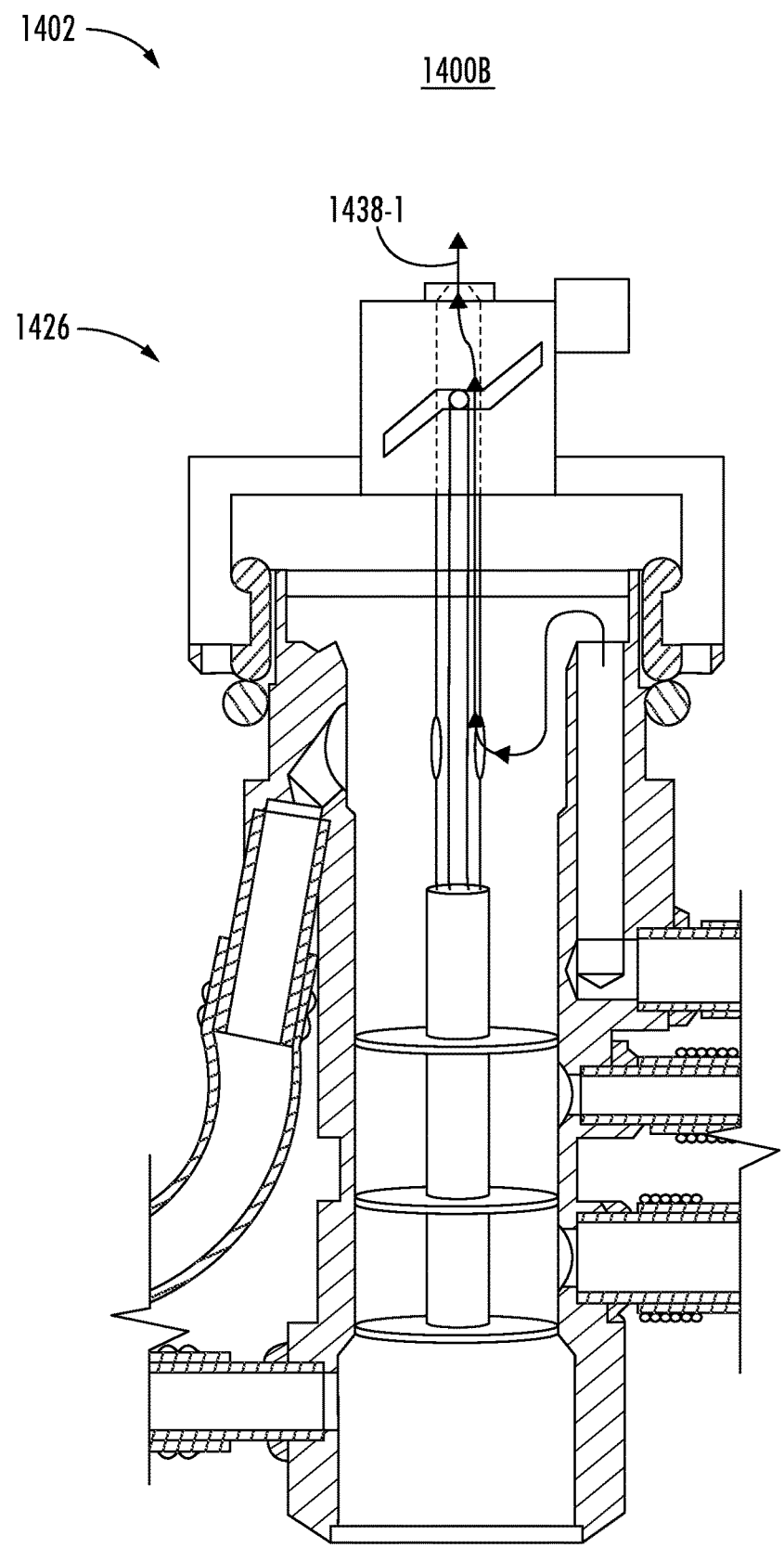
Figure 14C:
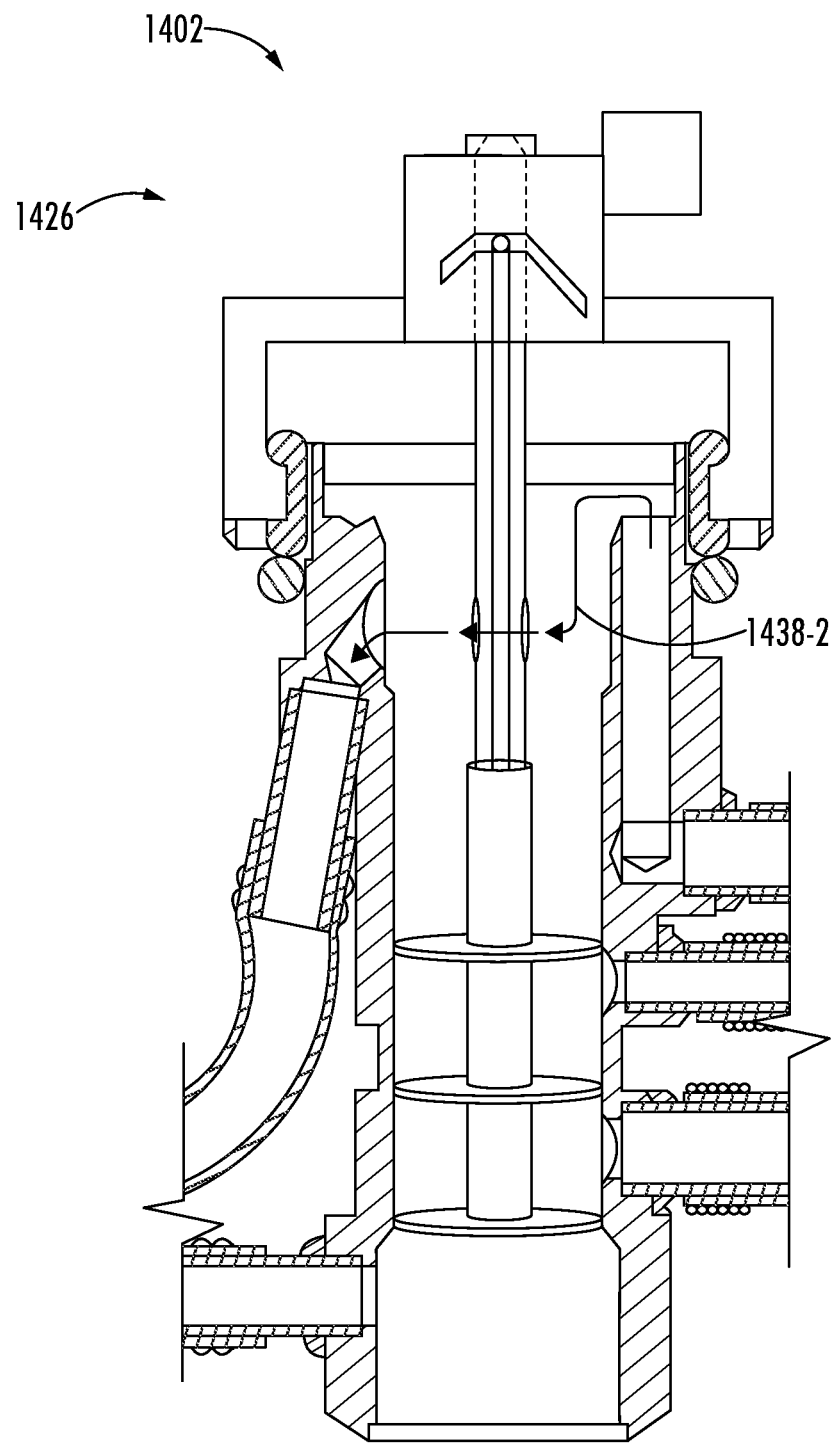

Referring to FIG. 14B, environment 1400B may illustrate an air escape state of AW valve assembly 1402. In the air escape state, flow 1438-1 may enter through the air input channel 1406, pass through the radial air hole 1466, enter interior channel 1421, and exit through the atmospheric channel 1416 at the top of AW valve well assembly 1402. Referring to FIG. 14C, environment 1400C may illustrate an air delivery state of AW valve assembly 1402. In the air delivery state, flow 1438-2 may enter through the air input channel 1406, pass through the interior channel 1421 via radial air hole 1466, and exit through the air output channel 1410. In various embodiments, the atmospheric channel 1416 may be blocked to transition from the air escape state to the air delivery state. In some embodiments, rotation of knob 1456 may cause the atmospheric channel 1416 to be blocked. In some such embodiments, knob 1456 may be depressed to control the position of the primary control valve 1420. In other embodiments, depressing knob 1456 may cause the atmospheric channel 1416 to be blocked. In still other embodiments, a finger may be placed over atmospheric channel 1416 to block it.

Figure 14D:
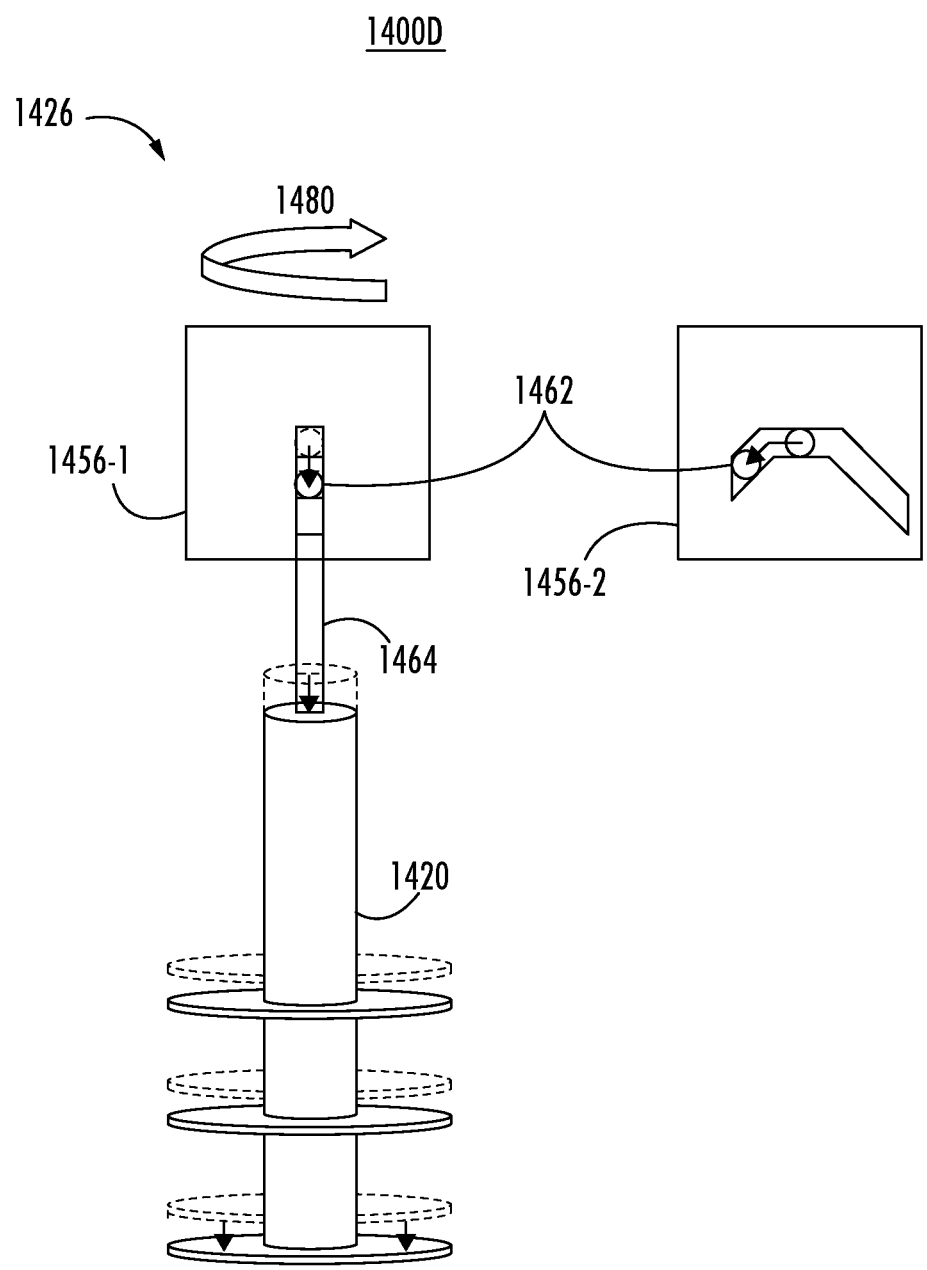

Referring to FIG. 14D, environment 1400D may illustrate aspects of AW valve assembly 1402 in a water delivery state. Knobs 1456-1, 1456-2 may illustrate front and side views of knob 1456, respectively. In the illustrated embodiment, clockwise 1480 rotation of knob 1456 may force cam pin 1462 to force primary control valve 1420 downward a first amount. In various embodiments, the downward motion of the primary control valve 1420 may place the water input channel 1408 in fluid communication with the water output channel 1412 and/or cause air input valve 1422 to block flow from air input channel 1406. In many embodiments, a biasing member may force air input valve 1422 against air input channel 1406 to block flow from air input channel 1406 in a manner similar to the manner illustrated and described with respect to FIG. 13.

Figure 14E:
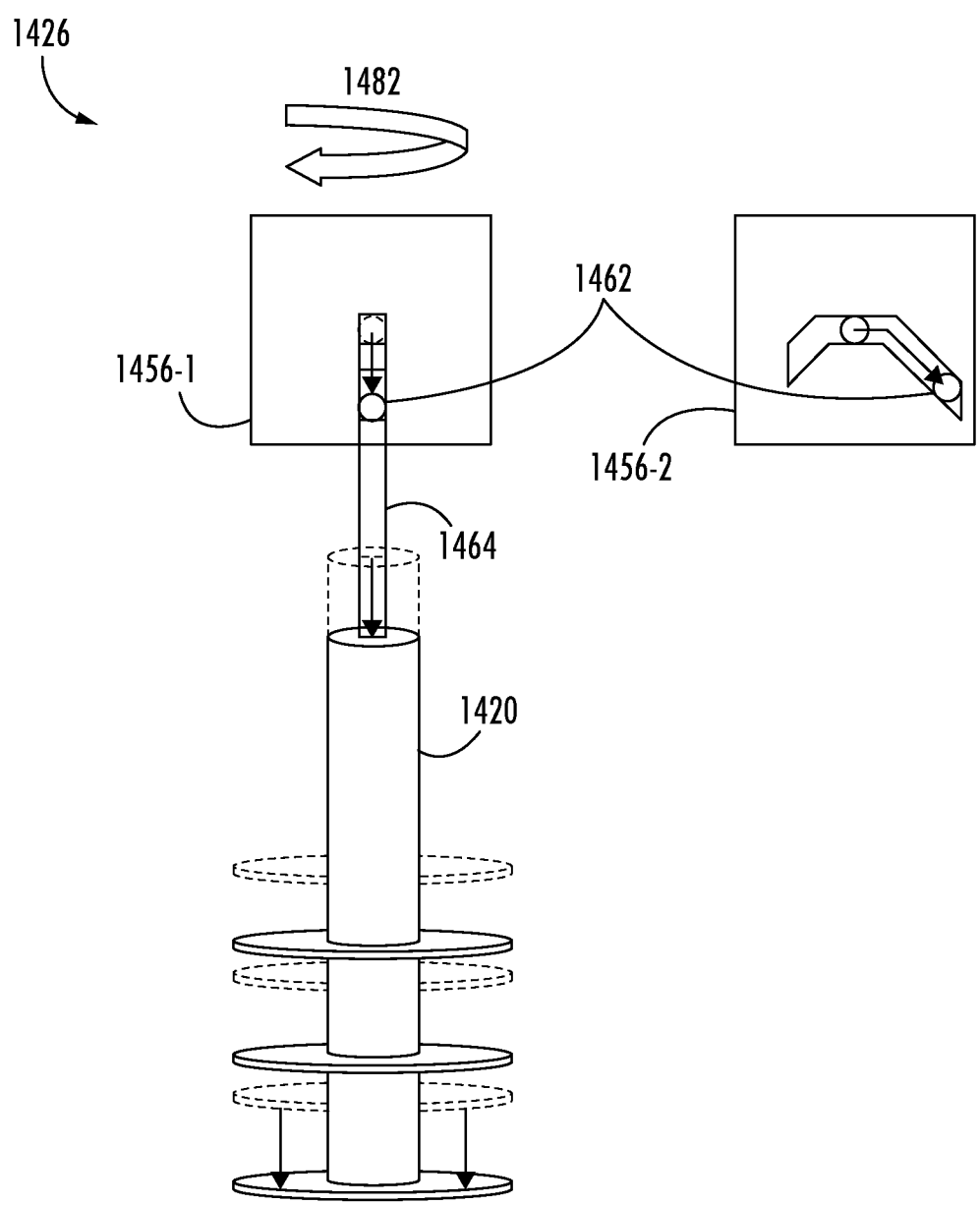

Referring to FIG. 14E, environment 1400E may illustrate aspects of AW valve assembly 1402 in a balloon fill state. Knobs 1456-1, 1456-2 may illustrate front and side views of knob 1456, respectively. In the illustrated embodiment, counterclockwise 1482 rotation of knob 1456 may force cam pin 1462 to force primary control valve 1420 downward a second amount, wherein the second amount is greater than the first amount. In various embodiments, the downward motion of the primary control valve 1420 may place the water input channel 1408 in fluid communication with the balloon channel 1414 and/or cause air input valve 1422 to block flow from air input channel 1406. In many embodiments, a biasing member may force air input valve 1422 against air input channel 1406 to block flow from air input channel 1406 in a manner similar to the manner illustrated and described with respect to FIG. 13.

The medical devices of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, EUS endoscopes, and the like. In various embodiments, the valve assemblies, or components thereof, described herein may include one or more (e.g., as a single or set of units) of a mounting point, mechanical coupler, bearing, seal, O-ring, actuator, valve, diaphragm, gasket, housing, connector, structural member, manifold, ergonomic features (e.g., finger/thumb grooves, padding, grip, application of mechanical advantage, and the like), spring, bellow, cantilever biasing member, torsional biasing member, linear biasing member, flapper valve, skirt, fin, disc, channel, cavity, lumen, and the like. In many embodiments, one or more components described herein may be constructed utilizing a variety of devices, technologies and/or processes, such as three-dimensional (3D) printing, multi-axis computer numeric control (CNC) machines, additive manufacturing, subtractive manufacturing, injection molding, computer aided design (CAD) programs, path planning programs, machining, forging, casting, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
    a valve set including a primary control valve, an air input valve, and an atmospheric valve, the primary control valve configured to control flow between a water input channel, a water output channel, and a balloon channel of a valve well, the air input valve configured to control flow through an air input channel of the valve well, and the atmospheric valve configured to control flow through an atmospheric channel;

a valve interface mechanism including a set of one or more biasing members and a user interface mechanism, the user interface mechanism comprising an interface member and a slot cam, the interface member operable between a first state, a second state, a third state, and a fourth state, the first state comprising the valve set configured to place the air input channel in fluid communication with the atmospheric channel, the second state comprising the valve set configured to place the air input channel in fluid communication with the air output channel, the third state comprising the valve set configured to place the water input channel in fluid communication with the water output channel, and the fourth state comprising the valve set configured to place the water input channel in fluid communication with the balloon channel, wherein in the first state the air input valve permits flow through the air input channel and the atmospheric valve permits flow through the atmospheric channel, wherein in the second state the air input valve permits flow through the air input channel and the atmospheric valve blocks flow through the atmospheric valve, wherein in the third state the primary control valve permits flow from the water input channel to the water output channel and the air input valve blocks flow through the air input channel, and wherein in the fourth state the primary control valve permits flow from the water input channel to the balloon channel and the air input valve blocks flow through the air input channel.

2. The medical device of claim 1, the slot cam configured to translate rotational motion of the interface member into linear motion of the primary control valve.

3. The medical device of claim 1, the user interface mechanism further comprising a cam pin and a linkage, the linkage to couple the cam pin to the primary control valve.

4. The medical device of claim 3, the cam pin to follow the slot cam to translate rotational motion of the interface member into linear motion of the primary control valve.

5. The medical device of claim 1, wherein a transition from one or more of the first state to the second state, the second state to the third state, and the third state to the fourth state produces tactile feedback via the interface member.

6. The medical device of claim 5, wherein the tactile feedback is created by different angles of different portions of the slot cam.

7. The medical device of claim 1, the set of one or more biasing members comprising a first biasing member to bias the primary control valve toward a top of the valve well.

8. The medical device of claim 7, the set of one or more biasing members comprising a second biasing member to couple the primary control valve to the air input valve.

9. The medical device of claim 1, the set of one or more biasing members comprising a biasing member to bias the air input valve against the air input channel in the third and fourth states.

10. The medical device of claim 9, the biasing member to prevent the air input valve from blocking the air input channel in the first and second states.

11. A medical device, comprising:

a valve set including a primary control valve, an air input valve, and an atmospheric valve, the primary control valve configured to control flow between a water input channel, a water output channel, and a balloon channel of a valve well, the air input valve configured to control flow through an air input channel of the valve well, and the atmospheric valve configured to control flow through an atmospheric channel;

a valve interface mechanism including a set of one or more biasing members and a user interface mechanism, the user interface mechanism comprising an interface member and a cam comprising a plurality of steps, the interface member operable between a first state, a second state, a third state, and a fourth state, the first state comprising the valve set configured to place the air input channel in fluid communication with the atmospheric channel, the second state comprising the valve set configured to place the air input channel in fluid communication with the air output channel, the third state comprising the valve set configured to place the water input channel in fluid communication with the water output channel, and the fourth state comprising the valve set configured to place the water input channel in fluid communication with the balloon channel, wherein in the first state the air input valve permits flow through the air input channel and the atmospheric valve permits flow through the atmospheric channel, wherein in the second state the air input valve permits flow through the air input channel and the atmospheric valve blocks flow through the atmospheric valve, wherein in the third state the primary control valve permits flow from the water input channel to the water output channel and the air input valve blocks flow through the air input channel, wherein in the fourth state the primary control valve permits flow from the water input channel to the balloon channel and the air input valve blocks flow through the air input channel, and wherein each of the second state, the third state, and the fourth state are associated with a different step of the plurality of steps.

* * * * *